(12) United States Patent
Pelo et al.

(10) Patent No.: US 8,337,537 B2
(45) Date of Patent: Dec. 25, 2012

(54) DEVICE FROM NATURALLY OCCURRING BIOLOGICALLY DERIVED MATERIALS

(75) Inventors: Mark Joseph Pelo, Macy, IN (US); Pamela Lynn Plouhar, South Bend, IN (US); Herbert Eugene Schwartz, Fort Wayne, IN (US); Prasanna Malaviya, Fort Wayne, IN (US); Terrence David Whalen, Leesburg, IN (US)

(73) Assignee: DePuy Products, Inc., Somerville, NJ (US)

( * ) Notice: Subject to any disclaimer, the term of this patent is extended or adjusted under 35 U.S.C. 154(b) by 1836 days.

(21) Appl. No.: 10/483,465

(22) PCT Filed: Jul. 15, 2002

(86) PCT No.: PCT/US02/23189
§ 371 (c)(1),
(2), (4) Date: Jan. 12, 2004

(87) PCT Pub. No.: WO03/007839
PCT Pub. Date: Jan. 30, 2003

(65) Prior Publication Data
US 2004/0220574 A1    Nov. 4, 2004

Related U.S. Application Data

(60) Provisional application No. 60/305,786, filed on Jul. 16, 2001, provisional application No. 60/389,028, filed on Jun. 14, 2002.

(51) Int. Cl.
*A61B 17/86* (2006.01)
(52) U.S. Cl. .......... 606/329; 606/75; 606/331; 606/321; 606/304

(58) Field of Classification Search ............ 606/72–73, 606/76–77, 232; 623/23.61, 23.63, 23.75
See application file for complete search history.

(56) References Cited

U.S. PATENT DOCUMENTS

| | | | |
|---|---|---|---|
| 3,272,204 A | | 9/1966 | Artandi et al. |
| 3,562,820 A | * | 2/1971 | Braun ................. 623/23.64 |
| 4,060,089 A | * | 11/1977 | Noiles ..................... 606/220 |
| 4,105,034 A | | 8/1978 | Shalaby et al. |
| 4,130,639 A | | 12/1978 | Shalaby et al. |
| 4,140,678 A | | 2/1979 | Shalaby et al. |
| 4,141,087 A | | 2/1979 | Shalaby et al. |
| 4,205,399 A | | 6/1980 | Shalaby et al. |
| 4,208,511 A | | 6/1980 | Shalaby et al. |

(Continued)

FOREIGN PATENT DOCUMENTS

EP    0 446 105 A2    1/1992

(Continued)

OTHER PUBLICATIONS

Hodde and Hiles, "Bioactive FGF-2 in sterilized extracellular matrix", Wounds, 13(5): 195-201 (2001).

(Continued)

*Primary Examiner* — Alvin Stewart
*Assistant Examiner* — Mary Hoffman

(57) ABSTRACT

Orthopaedic devices are disclosed. The devices include a part that is made of extracellular matrix material that has been hardened. One method of hardening the extracellular matrix is to comminute naturally occurring extracellular matrix and dry the comminuted material. The hardened extracellular matrix material can be machined to form a variety of orthopaedic devices.

15 Claims, 8 Drawing Sheets

U.S. PATENT DOCUMENTS

| | | |
|---|---|---|
| 4,352,463 A | 10/1982 | Baker |
| 4,400,833 A | 8/1983 | Kurland |
| 4,418,691 A | 12/1983 | Yannas et al. |
| 4,610,397 A | 9/1986 | Fischer et al. |
| 4,642,120 A | 2/1987 | Nevo et al. |
| 4,669,473 A | 6/1987 | Richards et al. |
| 4,703,108 A | 10/1987 | Silver et al. |
| 4,705,040 A | 11/1987 | Mueller et al. |
| 4,741,330 A | 5/1988 | Hayhurst |
| 4,750,492 A | 6/1988 | Jacobs |
| 4,846,835 A | 7/1989 | Grande |
| 4,873,976 A | 10/1989 | Schreiber |
| 4,880,429 A | 11/1989 | Stone |
| 4,902,508 A | 2/1990 | Badylak et al. |
| 4,919,667 A | 4/1990 | Richmond |
| 4,956,178 A | 9/1990 | Badylak et al. |
| 4,956,179 A | 9/1990 | Bamberg et al. |
| 4,976,715 A | 12/1990 | Bays et al. |
| 5,007,934 A | 4/1991 | Stone |
| 5,061,286 A | 10/1991 | Lyle |
| 5,102,421 A | 4/1992 | Anspach, Jr. |
| 5,108,438 A | 4/1992 | Stone |
| 5,128,326 A | 7/1992 | Balazs et al. |
| RE34,021 E | 8/1992 | Mueller et al. |
| 5,158,573 A | 10/1992 | Berg |
| 5,236,431 A | 8/1993 | Gogolewski et al. |
| 5,246,441 A | 9/1993 | Ross et al. |
| 5,258,015 A | 11/1993 | Li et al. |
| 5,264,214 A * | 11/1993 | Rhee et al. .................. 424/422 |
| 5,269,809 A | 12/1993 | Hayhurst et al. |
| 5,275,826 A | 1/1994 | Badylak et al. |
| 5,281,422 A | 1/1994 | Badylak et al. |
| 5,306,311 A | 4/1994 | Stone et al. |
| 5,320,633 A | 6/1994 | Allen et al. |
| 5,326,350 A * | 7/1994 | Li .............................. 623/23.72 |
| 5,329,846 A | 7/1994 | Bonutti |
| 5,350,583 A | 9/1994 | Yoshizato et al. |
| 5,352,463 A * | 10/1994 | Badylak et al. ............... 424/551 |
| 5,372,821 A | 12/1994 | Badylak et al. |
| 5,374,268 A | 12/1994 | Sander |
| 5,376,118 A | 12/1994 | Kaplan et al. |
| 5,380,334 A | 1/1995 | Torrier et al. |
| 5,445,833 A | 8/1995 | Badylak et al. |
| 5,447,940 A | 9/1995 | Harvey et al. |
| 5,460,962 A | 10/1995 | Kemp |
| 5,464,929 A | 11/1995 | Bezwada et al. |
| 5,479,033 A | 12/1995 | Baca et al. |
| 5,514,181 A | 5/1996 | Light et al. |
| 5,516,533 A | 5/1996 | Badylak et al. |
| 5,520,691 A | 5/1996 | Branch |
| 5,545,178 A | 8/1996 | Kensey et al. |
| 5,554,389 A | 9/1996 | Badylak et al. |
| 5,569,252 A | 10/1996 | Justin et al. |
| 5,571,193 A * | 11/1996 | Kampner .................. 623/23.57 |
| 5,573,784 A | 11/1996 | Badylak et al. |
| 5,591,234 A | 1/1997 | Kirsch |
| 5,593,441 A | 1/1997 | Lichtenstein et al. |
| 5,595,621 A | 1/1997 | Light et al. |
| 5,595,751 A | 1/1997 | Bezwada et al. |
| 5,597,579 A | 1/1997 | Bezwada et al. |
| 5,601,558 A | 2/1997 | Torrie et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,626,614 A | 5/1997 | Hart |
| 5,630,824 A | 5/1997 | Hart |
| 5,632,745 A | 5/1997 | Schwartz |
| 5,641,518 A * | 6/1997 | Badylak et al. ............... 424/551 |
| 5,645,850 A | 7/1997 | Bezwada et al. |
| 5,645,860 A | 7/1997 | Knapp, Jr. et al. |
| 5,648,088 A | 7/1997 | Bezwada et al. |
| 5,660,225 A | 8/1997 | Saffran |
| 5,668,288 A | 9/1997 | Storey et al. |
| 5,669,912 A | 9/1997 | Spetzler |
| 5,677,355 A | 10/1997 | Shalaby et al. |
| 5,681,353 A | 10/1997 | Li et al. |
| 5,693,085 A | 12/1997 | Buirge et al. |
| 5,695,998 A | 12/1997 | Badylak et al. |
| 5,698,213 A | 12/1997 | Jamiolkowski et al. |
| 5,700,583 A | 12/1997 | Jamiolkowski et al. |
| 5,702,462 A | 12/1997 | Oberlander |
| 5,711,960 A | 1/1998 | Shikinami |
| 5,711,969 A | 1/1998 | Patel et al. |
| 5,716,359 A * | 2/1998 | Ojima et al. .................... 606/76 |
| 5,725,556 A | 3/1998 | Moser et al. |
| 5,730,933 A | 3/1998 | Peterson |
| 5,733,337 A | 3/1998 | Carr, Jr. et al. |
| 5,733,868 A | 3/1998 | Peterson et al. |
| 5,735,897 A | 4/1998 | Buirge |
| 5,735,903 A | 4/1998 | Li et al. |
| 5,736,372 A | 4/1998 | Vacanti et al. |
| 5,753,267 A | 5/1998 | Badylak et al. |
| 5,755,791 A | 5/1998 | Whitson et al. |
| 5,759,190 A | 6/1998 | Vibe-Hansen et al. |
| 5,759,205 A | 6/1998 | Valentini |
| 5,759,208 A | 6/1998 | Valentini |
| 5,762,600 A | 6/1998 | Bruchman et al. |
| 5,762,966 A | 6/1998 | Knapp, Jr. et al. |
| 5,769,899 A | 6/1998 | Schwartz et al. |
| 5,773,577 A | 6/1998 | Cappello |
| 5,788,625 A | 8/1998 | Plouhar et al. |
| 5,795,353 A | 8/1998 | Felt |
| 5,800,537 A | 9/1998 | Bell |
| 5,830,708 A | 11/1998 | Naughton |
| 5,834,232 A | 11/1998 | Bishop et al. |
| 5,842,477 A | 12/1998 | Naughton et al. |
| 5,843,084 A * | 12/1998 | Hart et al. ........................ 606/77 |
| 5,847,012 A | 12/1998 | Shalaby et al. |
| 5,855,610 A | 1/1999 | Vacanti et al. |
| 5,855,613 A | 1/1999 | Antanavich et al. |
| 5,855,619 A | 1/1999 | Caplan et al. |
| 5,859,150 A | 1/1999 | Jamiolkowski et al. |
| 5,861,004 A | 1/1999 | Kensey et al. |
| 5,863,551 A | 1/1999 | Woerly |
| 5,866,414 A | 2/1999 | Badylak et al. |
| 5,885,619 A | 3/1999 | Patel et al. |
| 5,891,558 A | 4/1999 | Bell et al. |
| 5,899,939 A | 5/1999 | Boyce et al. |
| 5,905,997 A | 5/1999 | Stiles |
| 5,916,265 A | 6/1999 | Hu |
| 5,922,028 A | 7/1999 | Plouhar et al. |
| 5,939,323 A | 8/1999 | Valentini et al. |
| 5,948,429 A | 9/1999 | Bell et al. |
| 5,954,723 A | 9/1999 | Spetzler |
| 5,954,747 A | 9/1999 | Clark |
| 5,955,110 A | 9/1999 | Patel et al. |
| 5,958,874 A | 9/1999 | Clark et al. |
| 5,968,096 A | 10/1999 | Whitson et al. |
| 5,969,020 A | 10/1999 | Shalaby et al. |
| 5,971,987 A | 10/1999 | Huxel et al. |
| 5,980,524 A | 11/1999 | Justin et al. |
| 5,981,802 A | 11/1999 | Katz |
| 5,981,825 A | 11/1999 | Brekke |
| 5,989,269 A | 11/1999 | Vibe-Hansen et al. |
| 5,989,280 A | 11/1999 | Euteneuer et al. |
| 5,993,475 A | 11/1999 | Lin et al. |
| 5,993,844 A | 11/1999 | Abraham et al. |
| 5,997,575 A | 12/1999 | Whitson et al. |
| 6,010,525 A | 1/2000 | Bonutti et al. |
| 6,017,301 A | 1/2000 | Schwartz et al. |
| 6,017,348 A | 1/2000 | Hart et al. |
| 6,027,744 A | 2/2000 | Vacanti et al. |
| 6,034,140 A | 3/2000 | Schwartz et al. |
| 6,042,610 A | 3/2000 | Li et al. |
| 6,051,750 A | 4/2000 | Bell |
| 6,056,752 A | 5/2000 | Roger |
| 6,056,777 A | 5/2000 | McDowell |
| 6,056,778 A | 5/2000 | Grafton et al. |
| 6,060,640 A | 5/2000 | Pauley et al. |
| 6,066,160 A | 5/2000 | Colvin et al. |
| 6,068,648 A | 5/2000 | Cole et al. |
| 6,077,989 A | 6/2000 | Kandel et al. |
| 6,080,194 A | 6/2000 | Pachence et al. |
| 6,093,201 A | 7/2000 | Cooper et al. |
| 6,096,347 A | 8/2000 | Geddes et al. |
| 6,099,567 A | 8/2000 | Badylak et al. |
| 6,110,212 A | 8/2000 | Gregory |

| | | | |
|---|---|---|---|
| 6,126,686 A | 10/2000 | Badylak et al. | |
| 6,133,325 A | 10/2000 | Schwartz et al. | |
| 6,146,385 A | 11/2000 | Torrie et al. | |
| 6,152,935 A | 11/2000 | Kammerer et al. | |
| 6,153,292 A | 11/2000 | Bell et al. | |
| 6,156,044 A | 12/2000 | Kammerer et al. | |
| 6,165,225 A | 12/2000 | Antanavich et al. | |
| 6,171,344 B1 | 1/2001 | Atala | |
| 6,176,880 B1 | 1/2001 | Plouhar et al. | |
| 6,178,972 B1 | 1/2001 | Bell et al. | |
| 6,179,840 B1 | 1/2001 | Bowman | |
| 6,179,872 B1 | 1/2001 | Bell et al. | |
| 6,187,039 B1 | 2/2001 | Hiles | |
| 6,197,296 B1 | 3/2001 | Davies et al. | |
| 6,206,931 B1 | 3/2001 | Cook et al. | |
| 6,214,048 B1 | 4/2001 | Ito et al. | |
| 6,214,049 B1 | 4/2001 | Gayer et al. | |
| 6,224,892 B1 | 5/2001 | Searle | |
| 6,235,057 B1 | 5/2001 | Roger | |
| 6,242,247 B1 | 6/2001 | Rieser et al. | |
| 6,251,143 B1 * | 6/2001 | Schwartz et al. | 623/23.72 |
| 6,251,876 B1 | 6/2001 | Bellini et al. | |
| 6,258,124 B1 | 7/2001 | Darois et al. | |
| 6,264,702 B1 | 7/2001 | Ory et al. | |
| 6,265,333 B1 | 7/2001 | Dzenis et al. | |
| 6,267,957 B1 | 7/2001 | Green et al. | |
| 6,270,530 B1 | 8/2001 | Eldridge et al. | |
| 6,273,893 B1 | 8/2001 | McAllen, III et al. | |
| 6,280,473 B1 | 8/2001 | Lemperle et al. | |
| 6,280,474 B1 | 8/2001 | Cassidy et al. | |
| 6,283,980 B1 | 9/2001 | Vibe-Hansen et al. | |
| 6,288,043 B1 | 9/2001 | Spiro et al. | |
| 6,290,711 B1 | 9/2001 | Caspari et al. | |
| 6,293,961 B2 | 9/2001 | Schwartz et al. | |
| 6,294,041 B1 | 9/2001 | Boyce et al. | |
| 6,299,905 B1 | 10/2001 | Peterson et al. | |
| 6,306,140 B1 * | 10/2001 | Siddiqui | 606/315 |
| 6,306,156 B1 | 10/2001 | Clark | |
| 6,306,159 B1 | 10/2001 | Schwartz et al. | |
| 6,306,177 B1 | 10/2001 | Felt et al. | |
| 6,319,258 B1 | 11/2001 | McAllen, III et al. | |
| 6,319,271 B1 | 11/2001 | Schwartz et al. | |
| 6,326,025 B1 | 12/2001 | Sigler et al. | |
| 6,333,029 B1 | 12/2001 | Vyakarnam et al. | |
| 6,334,872 B1 | 1/2002 | Termin et al. | |
| 6,355,699 B1 | 3/2002 | Vyakarnam et al. | |
| 6,358,284 B1 | 3/2002 | Fearnot et al. | |
| 6,364,884 B1 | 4/2002 | Bowman et al. | |
| 6,371,958 B1 | 4/2002 | Overaker | |
| 6,373,221 B1 | 4/2002 | Koike et al. | |
| 6,379,367 B1 | 4/2002 | Vibe-Hansen et al. | |
| 6,379,710 B1 | 4/2002 | Badylak | |
| 6,383,221 B1 | 5/2002 | Scarborough et al. | |
| 6,387,693 B2 | 5/2002 | Rieser et al. | |
| 6,402,766 B2 | 6/2002 | Bowman et al. | |
| 6,409,764 B1 | 6/2002 | White et al. | |
| 6,423,073 B2 | 7/2002 | Bowman | |
| 6,436,110 B2 | 8/2002 | Bowman et al. | |
| 6,440,444 B2 | 8/2002 | Boyce et al. | |
| 6,447,517 B1 | 9/2002 | Bowman | |
| 6,451,032 B1 | 9/2002 | Ory et al. | |
| 6,458,158 B1 | 10/2002 | Anderson et al. | |
| 6,458,383 B2 | 10/2002 | Chen et al. | |
| 6,464,729 B1 | 10/2002 | Kandel | |
| 6,497,650 B1 | 12/2002 | Nicolo | |
| 6,497,707 B1 | 12/2002 | Bowman et al. | |
| 6,508,821 B1 | 1/2003 | Schwartz et al. | |
| 6,517,564 B1 | 2/2003 | Grafton et al. | |
| 6,566,345 B2 | 5/2003 | Miller et al. | |
| 6,572,650 B1 | 6/2003 | Abraham et al. | |
| 6,592,623 B1 | 7/2003 | Bowlin et al. | |
| 6,638,312 B2 | 10/2003 | Plouhar et al. | |
| 6,652,872 B2 | 11/2003 | Nevo et al. | |
| 6,666,892 B2 | 12/2003 | Hiles et al. | |
| 6,692,499 B2 | 2/2004 | Törmälä et al. | |
| 6,812,221 B2 | 11/2004 | McKeehan et al. | |
| 6,840,962 B1 | 1/2005 | Vacanti et al. | |
| 6,869,938 B1 | 3/2005 | Schwartz et al. | |
| 6,989,034 B2 | 1/2006 | Hammer et al. | |
| 2001/0002446 A1 | 5/2001 | Plouhar et al. | |
| 2001/0018614 A1 * | 8/2001 | Bianchi | 623/16.11 |
| 2001/0023373 A1 | 9/2001 | Plouhar et al. | |
| 2001/0024658 A1 | 9/2001 | Chen et al. | |
| 2001/0031254 A1 * | 10/2001 | Bianchi et al. | 424/93.7 |
| 2001/0043943 A1 | 11/2001 | Coffey | |
| 2002/0019649 A1 | 2/2002 | Sikora et al. | |
| 2002/0031551 A1 | 3/2002 | Peterson et al. | |
| 2002/0034533 A1 | 3/2002 | Peterson et al. | |
| 2002/0038151 A1 | 3/2002 | Plouhar et al. | |
| 2002/0048595 A1 | 4/2002 | Geistlich et al. | |
| 2002/0052628 A1 | 5/2002 | Bowman | |
| 2002/0090725 A1 * | 7/2002 | Simpson et al. | 435/402 |
| 2002/0095157 A1 | 7/2002 | Bowman | |
| 2002/0099448 A1 | 7/2002 | Hiles | |
| 2002/0165611 A1 | 11/2002 | Enzerink et al. | |
| 2002/0169465 A1 | 11/2002 | Bowman et al. | |
| 2002/0173806 A1 | 11/2002 | Giannetti et al. | |
| 2003/0014126 A1 | 1/2003 | Patel et al. | |
| 2003/0021827 A1 | 1/2003 | Malaviya et al. | |
| 2003/0023316 A1 | 1/2003 | Brown et al. | |
| 2003/0032961 A1 | 2/2003 | Pelo et al. | |
| 2003/0033021 A1 | 2/2003 | Plouhar et al. | |
| 2003/0033022 A1 | 2/2003 | Plouhar et al. | |
| 2003/0036797 A1 | 2/2003 | Malaviya et al. | |
| 2003/0036801 A1 | 2/2003 | Schwartz et al. | |
| 2003/0044444 A1 | 3/2003 | Malaviya et al. | |
| 2003/0049299 A1 | 3/2003 | Malaviya et al. | |
| 2003/0078617 A1 | 4/2003 | Schwartz et al. | |
| 2003/0212447 A1 | 11/2003 | Euteneuer et al. | |
| 2004/0059431 A1 | 3/2004 | Plouhar et al. | |
| 2004/0137042 A1 * | 7/2004 | Hiles et al. | 424/443 |
| 2004/0143344 A1 | 7/2004 | Malaviya et al. | |
| 2004/0166169 A1 | 8/2004 | Malaviya et al. | |
| 2004/0220574 A1 | 11/2004 | Pelo et al. | |
| 2005/0027307 A1 | 2/2005 | Schwartz et al. | |
| 2005/0249771 A1 | 11/2005 | Malaviya et al. | |
| 2005/0249772 A1 | 11/2005 | Malaviya et al. | |

FOREIGN PATENT DOCUMENTS

| | | |
|---|---|---|
| EP | 0591991 A2 | 4/1994 |
| EP | 0632999 A1 | 11/1995 |
| EP | 0 734 736 A1 | 10/1996 |
| EP | 1070487 | 1/2001 |
| EP | 1593400 A1 | 11/2005 |
| FR | 2422386 | 4/1978 |
| GB | 2 215 209 | 9/1989 |
| JP | 5200050 | 8/1993 |
| JP | 11319068 A | 11/1999 |
| JP | 2000506408 | 5/2000 |
| JP | 200161851 | 10/2001 |
| WO | WO 90/09769 | 9/1990 |
| WO | 9315721 | 8/1993 |
| WO | WO 94/11008 | 5/1994 |
| WO | 9504710 | 2/1995 |
| WO | WO 95/05083 | 2/1995 |
| WO | WO 95/22301 | 8/1995 |
| WO | WO 95/06439 | 9/1995 |
| WO | WO 95/32623 | 12/1995 |
| WO | W096/24304 | 8/1996 |
| WO | WO 96/24661 | 8/1996 |
| WO | WO 97/05193 | 2/1997 |
| WO | 9715195 | 5/1997 |
| WO | WO 97/37613 | 10/1997 |
| WO | WO 98/06445 | 2/1998 |
| WO | 9822154 | 5/1998 |
| WO | WO 98/22158 A2 | 5/1998 |
| WO | WO 98/22158 A3 | 5/1998 |
| WO | WO 98/30167 | 7/1998 |
| WO | WO 98/34569 | 8/1998 |
| WO | WO 98/40111 | 9/1998 |
| WO | WO 99/03979 | 1/1999 |
| WO | 9919005 | 4/1999 |
| WO | WO 99/43786 | 9/1999 |
| WO | WO 99/47188 | 9/1999 |
| WO | WO 00/15765 | 3/2000 |
| WO | WO 00/16822 | 3/2000 |
| WO | WO 00/24437 A2 | 5/2000 |
| WO | WO 00/24437 A3 | 5/2000 |

| | | |
|---|---|---|
| WO | WO 00/32250 | 6/2000 |
| WO | WO 00/48550 | 8/2000 |
| WO | WO 00/72782 | 12/2000 |
| WO | WO 01/19423 | 3/2001 |
| WO | WO 01/39694 A2 | 6/2001 |
| WO | WO 01/39694 A3 | 6/2001 |
| WO | WO 01/45765 | 6/2001 |
| WO | WO 01/66159 | 9/2001 |
| WO | WO 02/22184 | 3/2002 |
| WO | WO 03/007784 | 1/2003 |
| WO | WO 03/007788 A2 | 1/2003 |
| WO | WO 03/007790 A2 | 1/2003 |

OTHER PUBLICATIONS

O'Meara, Patrick, "The basic science of meniscus repair," Orthopaedic review, Jun. 1993, pp. 681-686.
Clearfix screw advertisement, 1998, Innovative devices, Inc.
Winters and Justin, "Clearfix meniscal screw", Innovative devices, Inc. 1998.
Surgical dynamics, meniscal stapler advertisement, 1997.
Bionix implants, Meniscus arrow advertisement, 1996.
Instrument maker, inc., Meniscus mender II, 1989.
William G. Clancy, Jr., M.D., and Ben K. Graf, M.D., "Arthroscopic Meniscal Repair," ACUFEX Microsurigal Inc., advertisement, 1988.
Supplementary European Search Report, Appln No. 02753403.1 (PCT/US 223190) dated Dec. 21, 2006 (3 pages).
Definitions of "intertwine" and "twine." American Heritage Dictionary of the English Language Online. Accessed Sep. 29, 2005. 2 pages.
On-line Medical Dictionary definition of "extracellular matrix" located at http://cancerweb.ncl.ac.uk/cgibin/omd?extracellular+matrix.
P. K. Chu et al., "Plasma-surface modification of biomaterials", Materials Science and Engineering, Reports: A Review Journal, vol. 36, No. 5-6, Mar. 29, 2002, pp. 143-206.
Arnoczky et al, The microvasculature of the meniscus and its response to injury—An experimental study in the dog, Am. J. Sports Med., 1983, 11(3); pp. 131-141.
Fox et al., Trephination of incomplete meniscal tears, Arthroscopy, 1993, 9(4); pp. 451-455.
Arnoczky et al., Meniscal repair using an exogenous fibrin clot—An experimental study of dogs, J. Bone Joint Surg. Am., 1988, 70(8), pp. 1209-1218.
Rodeo, "Arthroscopic meniscal repair with use of the outside-in technique", Instr. Course Lect., 2000, 49, pp. 195-206.
Stollsteimer et al., "Meniscal allograft transplantation: a 1- to 5-year follow-up of 22 patients", Arhroscopy, 2000, 16(4), pp. 343-347.
Rodeo, "Meniscal allografts—where do we stand?", Am. J. Sports Med., 2001, 29(2), pp. 246-261.
Sweigart at al., "Toward tissue engineering of the knee meniscus", Tissue Eng., 2001, 7(2), pp. 111-129.
Boss at al., "Technical innovative: creation of a peripheral vascularized trough to enhance healing in cryopreserved meniscal allograft reconstruction", Knee Surg Sports Traumatol Arthrosc., 2000, 8(3), pp. 159-162.
Siegel et al., "Meniscal allografts", Clin Sports Med., 1993, 12(1), pp. 59-80.
Klompmaker et al., "Meniscal replacement using a porous polymer prosthesis: a preliminary study in the dog.", Biomaterials, 1996, 17(12), pp. 1169-1175.
de Groot et al., "Use of porous polyurethanes for maniacal reconstruction and meniscal protheses", Biomaterials, 1996, 17(2), pp. 163-173.
Spaans et al., "Solvent-free fabrication of micro-porous polyurethane amide and polyurethane-urea scaffolds for repair and replacement of the knee-joint meniscus", Biomaterials, 2000, 21(23), pp. 2453-2460.
Stone et al., "Regeneration of meniscal cartilage with use of a collagen scaffold—Analysis of Preliminary data", J. Bone Joint Surg. Am., 1997, 79(12), pp. 1770-1777.
Rodkey et al., "A clinical study of collagen meniscus implants to restore the injured meniscus", Clin. Orthop., 1999, 49(367 Suppl.), pp. S281-S292.

Merriam-Webster Online Dictionary definitions of "suspension", "suspend", "cohesive", "cohesion", "comminute", "pulverize", "submucosa", and "tissue". Accessed Mar. 30, 2006, 9 pgs.
Resin Technology Group, LLC, "Viscosity chart", http://www.resintechgroup.com/tables/viscosity.html, accessed online Mar. 30, 2006, 1 pg.
Definitions from Onelook.com for "trimethylen" and "trimethylene".
J.S. Pieper et al "Preparation and characterization of porous crosslinked collagenous matrices containing bioavailable chondroitin suplhate" Biomaterials 1999, 20: 847-858.
P.B. van Wachem et al. "In vivo biocompatability of carbodiimide-crosslinked collagen matrices: Effects of crosslink density, heparin immobilization, and bFGF loading" J. Biomed. Mater. Res. 2001, 55 (3): 368-378.
Kyumin Whang "A biodegradable polymer scaffold for delivery of osteotropic factors" Biomaterials 2000, 21 (24): 2545-2551.
J.S. Pieper et al. Attachment of glycosaminoglycans to collangenous matrices modulates the tissue response in rats, Biomaterials 2000, 21 (16): 1689-1699.
Kristen Billiar et al. "Effects of carbodiimide crosslinking conditions on the physical properties of laminated intestinal submucosa", J. Biomed. Mater. Res. 2001, 51(1): 101-108.
Toshimitsu Momose et al. "Surface modification of extrasynovial tendon by chemically modified hyaluronic acid coating" J. Biomed. Mater. Res. 2002, 59: 219-224.
Handbook of Biodegradable Polymers Hardwood Press 1997 (251-272).
Cohn at al., "Biodegradable PEO/PLA block copolymers," Journal of Biomedical Materials Research, 1988, 22 (993-1009).
"Polymer Preprints" (ACS Division of Polymer Chemistry), 1989. 30 (1): 498.
The Encyclopedia of Polymer Science, 1988 (13) 31-41.
"Handbook of Biodegradable Polymers" Hardwood Press 1977 (161-182).
"Handbook of Biodegradable Polymers" Hardwood Press 1997 (99-118).
Disilvestro et al., "Effects of Cross-Linking on the Mechanical Properties of a Porous Foam Scaffold of Small Intestine Submucosa", Society for Biomaterials 29th Annual Meeting Transactions, 2003, pp. 88.
Ide et al., "Collagen Hybridization with Poly(I-Lactic Acid) Braid Promotes Ligament Cell Migration", Mater. Sci. Eng. C, 17(1-2), 95-99 (2001).
Bercovy et al., "Carbon-PGLA Prosthesis for Ligament Reconstruction Experimental Basis and Short Term Results in Man", Clin. Orthop. Relat. Res., (196), 159-68 (1985).
Zhu et al, "Immobilization of Biomacromolecules onto Aminolyzed Poly(L-lactic acid) toward Acceleration of Endothelium Regeneration", Tissue Engineering, v 10, pp. 53-61, 2004.
Cheng & Teoh, "Surface modification of ultra thin poly (ÿ caprolactone) films using acrylic acid and collagen", Biomaterials, v25(11), pp. 1991-2001, 2004.
Wan et al., "Cell adhesion on gaseous plasma modified poly-(L-lactide) surface under shear stress field", Biomaterials, v24(21), pp. 3757-3764, 2003.
Yang et al., "Effect of surface treatment on the biocompatibility of microbial polyhydroxyalkanoates", Biomaterials, v 23 (5), pp. 1391-1397, 2002.
Croll at al., "Controllable surface modification of Poly(lactic-co-glycolic acid) (PLGA) by hydrolysis or aminolysis I: physical, chemical, and theoretical aspects", Biomacromolecules, Mar.-Apr. 2004, 5(2): 463-473.
Kwon et al., "Fibroblast culture on surface-modified poly (glycolide-co-ÿ-caprolactone) scaffold for soft tissue regeneration", J. Biomater Sci Polym ed. 2001, 12(10) 1147-60.
Gastel JA, Muirhead WR, Lifrak JT, Fadale PD, Hulstyn MJ, Labrador DP "Meniscal tissue regeneration using a collagenous biomaterial derived from porcine small intestine submucosa", Arthroscopy, Feb.; 17(2): 151-159.
Tan W, Krishnaraj R, Desai TA "Evaluation of nanostructured composite collagen-chitosan matrices for tissue engineering", Tissue Eng Apr.; 7(2): 203-210, 2001.

Arnoczky SP "Building a meniscus", Biological considerations, Clin Orthop Oct.; 367 (suppl), S244-53, 1999.

Metcalf et al., "Surgical technique for xenograft (SIS) augmentation of rotator-cuff repairs", Op Tech Orthop, 12(3): 204-208, 2002.

Courtney et al., "Modification of polymer surfaces: optimization of approaches", Perfusion, v 18 (11), pp. 33-39, 2003.

Zhang et al., Design of nanostructured biological materials through self-assembly of peptides and proteins. MIT Current Opinion in chemical Biology, 2002, 6:865-871.

Friess, "Collagen in drug delivery and tissue engineering", *Advanced Drug Delivery Reviews*, vol. 55, No. 12, 2003, pp. 1529-1530.

Olsen et al., "Recombinant collagen and gelatin for drug delivery", *Advanced Drug Delivery Reviews*, vol. 55, No. 12, 2003, pp. 1547-1567.

Aigner et al., "Collagens-major component of the physiological cartilage matrix, major target of cartilage degeneration, major tool in cartilage repair", *Advanced Drug Delivery Reviews*, vol. 55, No. 12, 2003, pp. 1569-1593.

Geiger et al., "Collagen sponges for bone regeneration with rhBMP-2", *Advanced Drug Delivery Reviews*, vol. 55, No. 12, 2003, pp. 1613-1629.

Ruszczak et al., "Collagen as a carrier for on-site delivery of antibacterial drugs", *Advanced Drug Delivery Reviews*, vol. 55, No. 12, 2003, pp. 1679-1698.

O'Grady et al., "Global regulatory registration requirements for collagen-based combination products: points to consider", *Advanced Drug Delivery Reviews*, vol. 55, No. 12, 2003, pp. 1699-1721.

Matthews et al., "Electrospinning of Collagen Type II: A Feasibility Study", *Journal of Bioactive and Compatible Polymers*, vol. 18, Mar. 2003, pp. 125-134.

Biscarini et al., "Growth of High Vacuum Sublimed Oligomer Thin Films", *ACS Polymer Preprints*, vol. 37, No. 2, 1996, pp. 618-619.

Biscarini et al., "Morphology and roughness of high-vacuum sublimed oligomer thin films", *Thin Solid Films*, vol. 439-443, 1996, pp. 284-285.

Biscarini et al., "Scaling Behavior of Anisotropic Organic Thin Films Grown in High-Vacuum", *Physical Review Letters*, vol. 78, No. 12, Mar. 24, 1997, pp. 2389-2392.

Voytik-Harbin et al., "Identification of Extractable Growth Factors from Small Intestinal Submucosa", *Journal of Cellular Biochemistry*, vol. 67, 1997, pp. 478-491.

McPherson, Ph.D. et al., "Characterization of Fibronectin Derived from Porcine Small Intestinal Submucosa", *Tissue Engineering*, vol. 4, No. 1, 1998, pp. 75-83.

Hodde, et al., "Vascular Endothelial Growth Factor in Porcine-Derived Extracellular Matrix", *Endothelium*, vol. 8(1), 2001, pp. 11-24.

Hodde et al., "Wounds: A Compendium of Clinical Research and Practice", Website: http:www.hmpcommunications.com/WNDS, Printed: Jul. 12, 2005, 7 pgs.

Hurst et al., "Mapping of the distribution of significant proteins and proteoglycans in small intestinal submucosa by fluorescence microscopy", *J. Biomater. Sci. Polymer Edn.*, vol. 12, No. 11, 2001, pp. 1267-1279.

Hodde et al., "Fibronectin peptides mediate HMEC adhesion to porcine-derived extracellular matrix", *Biomaterials*, vol. 23, 2002, pp. 1841-1848.

Hodde, "Naturally Occurring Scaffolds for Soft Tissue Repair and Regeneration", *Tissue Engineering*, vol. 8, No. 2, 2002, pp. 295-308.

Allman et al., Xenogeneic Extracellular Matrix Grafts Elicit a Th2-Restricted Immune Response, *Transplantation*, vol. 71, No. 11, Jun. 15, 2001, pp. 1631-1640.

Allman et al., "The Th2-Restricted Immune Response to Xenogeneic Small Intestinal Submucosa Does Not Influence Systemic Protective Immunity to Viral and Bacterial Pathogens", *Tissue Engineering*, vol. 8, No. 1, 2002, pp. 53-62.

Krëma, "Nonwoven Textiles", *Textile Trade Press*, Manchester, England, 1962, 6 pgs.

Answers.com,. Definition of "freeze-dry", Accessed on May 12, 2005, 6 pgs.

Ma et al., "Microtubular architecture of biodegradable polymer scaffolds", *J. Biomed. Materials Res.*, vol. 56, No. 4, 2001, pp. 469-477.

Ma et al., "Biodegradable Polymer Scaffolds with Well-Defined Interconnected Spherical Pore Network", *Tissue Engineering*, vol. 7, No. 1, 2001, pp. 23-33.

Klawitter et al., "An Evaluation of Bone Growth into Porous High Density Polyethylene", *J. Biomed. Materials Res.*, vol. 10, (1976) pp. 311-323.

White et al., "Biomaterial Aspects of Interpore-200 Porous Hydroxyapatite", *Dental Clinics of North America*, Reconstructive Implant Surgery and Implant Prosthodontics 1, vol. 30, No. 1, pp. 49-67.

Shors, Coralline Bone Graft Substitutes, *Orthopaedic Clinics of North America*, Bone Grafting and Bone Graft Substitutes, vol. 30, No. 4, Oct. 1999, pp. 599-613.

Wang, Experimental Study of Osteogenic Activity of Sintered Hydroxyapatite—On the Relationship of Sintering Temperature and Pore Size—*J. Jpn. Orthop. Assoc.*, vol. 64, 1990, pp. 847-859.

Nehrer et al., "Matrix collagen type and pore size influence behavior of seeded canine chondrocytes", *Biomaterials*, vol. 18, No. 11, 1997, pp. 769-776.

Salem et al., "Interactions of 3T3 fibroblasts and endothelial with defined pore ffeatures", *J. Biomed Materials Res.*, vol. 61, No. 2, 2002, pp. 212-217.

Definitions of "intertwine" and "twine", *American Heritage Dictionary of the English Language Online*, Accessed Sep. 29, 2005, 2 pgs.

How to Cut Meat Products 2001, *Urschel Corp.*, Accessed online at fr.urschel.com/literature/HTCMeat.pdf on Oct. 3, 2005, 8 pgs.

Definitions of "comminute" and "slurry", Dictionary.com; Accessed Sep. 20, 2005, 2 pgs.

Hiles et al., "Mechanical properties of xenogeneic small-intestinal submucosa when used as an aortic graft in the dog", *Journal of Biomedical Materials Research*, vol. 29, 883-891, (1995).

Sandusky, et al., "Healing Comparison of Small Intestine Submucosa and ePTFE Grafts in the Canine Carotid Artery", *J. Surg.Res.*, 58:415-420, (1995).

Knapp, et al., "Biocompatibility of Small-Intestine Submucosa in Urinary Tract as Augmentation Cystoplasty Graft and Injectable Suspension". *J Endourology*, 8:125-130. (1994).

Kropp et al., "Regenerative Bladder Augmentation: A Review of the Initial Preclinical Studies with Porcine Small Intestinal Submucosa", *Muscle, Matrix, and Bladder Function*, Plenum Press. New York (1995).

Kropp et al., "Experimental Assessment of Small Intestinal Submucosa as a Bladder Wall Substitute", *Urology* 446:396-400, (1995).

Vaught et al., "Detrusor Regeneration in the Rat Using Porcine Small Intestinal Submucosa Grafts: Functional Innervation and Receptor Exoression", *J. Urol.*, 155:374-378, (1996).

Kropp et al, Characterization of Small Intestinal Submucosa Regenerated Canine Detrusor: Assessment of Reinnervation, in Vitro Compliance and contractility, *J. of Urol.* 156:599-607. (1996).

Kropp et al., "Regenerative Urinary Bladder Augmentation Using Small Intestinal Submucosa: Urodynamic and Histopathologic Assessment in Long-Term Canine Bladder Augmentations" *Journal of Urology*, 155:2098-2104 (1996).

Aiken et al., "Small Intestinal Submucosa as an Intra-Articular Ligamentous Graft Material: A Pilot Study in Dogs", *Vet Comp Orthooedics Traumatology*, 7:124-128. (1994).

Badylak et al., "The Use of Xenogeneic Small Intestinal Submucosa as a Biomaterial for Achille's Tendon Repair in a dog model" *J Biomed Materials.*29:977-985, (1995).

Hodde et al., "The Effect of Range of Motion Upon Remodeling of Small Intestinal Submucosa (SIS) when used as an Achilles Tendon Repair Material in the Rabbit", *Tissue Engineering* 3, 1:27-37, (1997).

Ferrand et al., "Directional Porosity of Porcine Small-Intestinal Submucosa", *J Biomed Materials Res*, 27:1235-1241, (1993).

Hiles et al., "Porosity of Porcine Small-Intestinal Submucosa for use as a Vascular Graft", *J Biomed Materials Res*, 27: 139-144. (1993).

Hodde et al., "Glycosaminoglycan Content of Small Intestinal Submucosa: A Bioscaffold for Tissue Replacement", *Tissue Engineering*, 2:3, 209-217, (1996).

Prevel et al., "Small Intestinal Submucosa: Utilization for Repair of Rodent Abdominal Wall Defects", *Ann Plast Surg*, 35:374-380, (1995).

Clarke et al., "Intestine Submucosa and Polypropylene Mesh for Abdominal Wall Repair in Dogs", *J Surg Res*, 60:107-114, (1996).

Prevel et al., "Small Intestinal Submucosa: Utilization as a Wound Dressing in Full-Thickness Rodent Wounds", *Ann Plast Surg.* 35:381-388, (1995).

Cobb et al., "Histology after Dural Grafting with Small Intestinal Submucosa", *Surgical Neurology*, 46: 389-394, (1996).

Cobb et al., "Porcine Small Intestinal Submucosa as a Dural Substitute", *Surgical Neurology*, 51:99-104, (1999).

Voytik-Harbin et al., "Application and Evaluation of the AlamarBlue Assay for Cell Growth and Survival of Fibroblasts", *Journal of Immunological Methods, in Vitro Cell Bio-Animal*, 34: 2399-246 (1998).

Suckow, M.A., "Enhanced Bone Regeneration Using Porcine Small Intestinal Submucosa", *J. Invest Surg*, 12: 277, (1999).

Badylak , S., et al., "Naturally Occurring Extracellular Matrix as a Scaffold for Musculoskeletal Repair", *Clin Orthop*, 3675:S333-S3433, (1999).

Cook, J.L. et al., "Induction of Meniscal Regeneration in Dogs Using a Novel Biomaterial", *Am J Sports Med*, 27: 658, (1999).

Dejardin, L.M. et al., "Use of small intestinal submucosal implants for regeneration of large fascial defects: an experimental study in dogs", *J Biomed Mater Res*, 46:203-211, (1999).

Sacks, M.S., et al., "Quantification of the fiber architecture and biaxial mechanical behavior of porcine intestinal submucosa", *J Biomed Mater Res*, 46:1-10, (1999).

COOK® News Releases, "COOK® Introduces Innovative Surgisis™ Soft Tissue Repair Biomaterial", (May 21, 2000).

COOK® News Releases, "COOK® Oasis ™ Wound Dressing Biomaterial From COOK® Remodels Partial Thickness Skin Injuries", (Dec. 23, 1999).

COOK® News Releases, "Cook Incorporated Forms Dedicated Tissue Engineered Products Group", (Feb. 16, 2000).

COOK® News Releases, "FDA Clears Oasis™ Wound Dressing Biomaterial From COOK® for Full-Thickness Skin Injuries", (Jan. 24, 2000).

Klootwyk, et al., "The Use of Xenographic SIS as a Biomaterial for Achilles Tendon Repair in Dogs," First SIS Symposium, Dec. 1996, USA.

Lenz, et al., "SIS as an ACL Replacement in Dogs and Goats," First Symposium, Dec. 1996, USA.

Cook, et al., "Comparison of SIS Cancellous Bone as Substrates for Three-Dimensional Culture of Canine Articular Chondrocytes," First SIS Symposium, Dec. 1996, USA.

Badylak, et al., "Different Configurations of Small Intestinal Submucosa as a Biomaterial for Achilles Tendon Repair in a Dog Model," First SIS Symposium, Dec. 1996, USA.

Voytik-Harbin & Badylak, "Induction of Osteogenic Activity by Small Intestinal Submucosa in Rat Calvaria Non-union Defects," First SIS Symposium, Dec. 1996, USA.

Kandel, et al., "SIS and Reconstituted Cartilage and Its Use in Joint Resurfacing of Focal Defects in Rabbits," First SIS Symposium, Dec. 1996, USA.

Tullius, et al., "Differential Permeabilty of SIS," First SIS Symposium, Dec. 1996, USA.

Obermiller, et al., "Suture Retention Strength of SIS," First SIS Symposium, Dec. 1996, USA.

Shelton, et al., "Repair of the Canine Medial Meniscus using SIS: A Feasibility Study," Second SIS Symposium, Dec. 1998, USA.

Cook, et al., "Meniscal Regeneration in dogs Using Grafts of SIS," Second SIS Symposium, Dec. 1998, USA.

Welch, et al., "Healing of Canine Meniscal Defect with Small Intestinal Submucosa Implants," Dec. 1998, USA.

Solchaga, et al., "SIS as Delivery Vehicle for Mesenchymal Progenitor Cells," Dec. 1998, USA.

Paulino, et al., "The Use of an SIS-PGA Composite Graft for Repair of Cartilage Defect," Dec. 1998, USA.

Toombs and May, "Clinical Follow-Up of Three Canine ACL Reconstructions Using an SIS ACL Device," Dec. 1998, USA.

Tomasek and Gifford, "Small Intestinal Submucosa Matrix Regulates the Differentiation of Myofibroblasts," Third SIS Symposium, Nov. 2000, USA.

Cook, et al., "Tissue Engineering for Meniscal Repair Using SIS," Third SIS Symposium, Nov. 2000, USA.

Lifrak, et al., "Enhanced Repair of Goat Meniscal Defects Using Porcine Small Intestinal Submucosa (SIS)," Third SIS Symposium, Nov. 2000, USA.

Hoffman, "SIS Disc Replacement for the Temporomandibular Joint," Third SIS Symposium, Nov. 2000, USA.

Kaeding, "Use of SIS in the Surgical Treatment of Chronic Symptomatic Patella Tendinosis," Third SIS Symposium, Nov. 2000, USA.

Tomczak and Kaeding, "Use of SIS in the Surgical Treatment of Tendinosis About the Foot and Ankle," Third SIS Symposium, Nov. 2000, USA.

Moore, et al., "Bridging Segmental Defects in Long Bones With Intramedullary Tubes and Periosteal Sleeves Made From Small Intestinal Submucosa (SIS)," Third SIS Symposium, Nov. 2000, USA.

Wang, et al., "Small Intestinal Submucosa Enhances Healing of Medical Collateral Ligament in a Rabbit Model," Third SIS Symposium, Nov. 2000, USA.

Ojha, et al., "PGA-Plla Versus Small Intestinal Submucosa (SIS): A Comparison of Neo-Cartilage Grown From Two Scaffold Materials," Third SIS Symposium, Nov. 2000, USA.

Wiklerson, "Use of the Porcine Small Intestine Submucosal Tissue Graft and Repair of Rotator Cuff Tears," Third SIS Symposium, Nov. 2000, USA.

"Small Intestinal Submucosa," Third SIS Symposium, Nov. 2000, USA.

"Current Clinical Applications of SIS," Third SIS Symposium, Nov. 2000, USA.

Hodde, et al., "Glycosaminoglycan Content of Small Intestinal Submucosa: A Potential for GAG-Growth Interactions in SIS-Mediated Healing", First Symposium, Dec. 1996, USA.

European Search Report for European Application No. 02756565.4-1219, Mar. 21, 2007, 5pgs.

European Search Report for European Patent Application No. 02747021.0-1219 / PCT/US0222411, Mar. 16, 2007, 6 pgs.

European Search Report for European Patent Application No. 02747021.0-1219, Jul. 17, 2007, 7 pgs.

European Search Report for European Patent Application No. 02750033.9-1219, Jul. 20, 2007, 6 pgs.

* cited by examiner

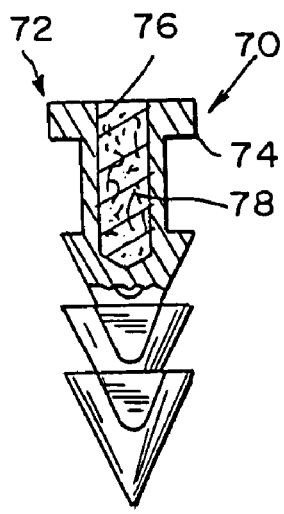
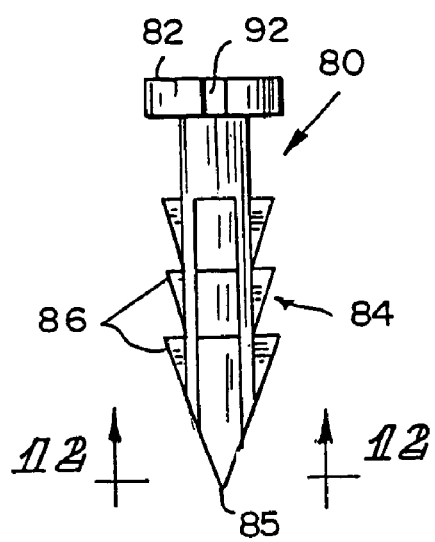
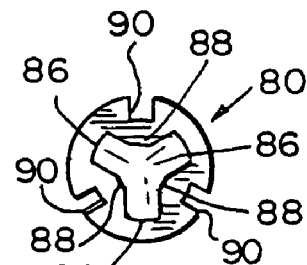
FIG. 10  FIG. 11  FIG. 12
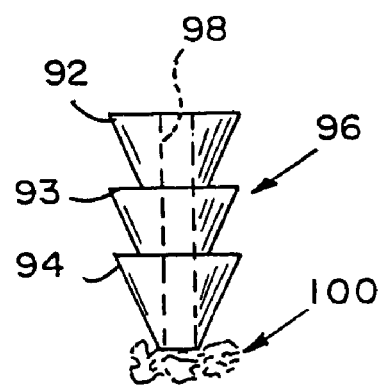
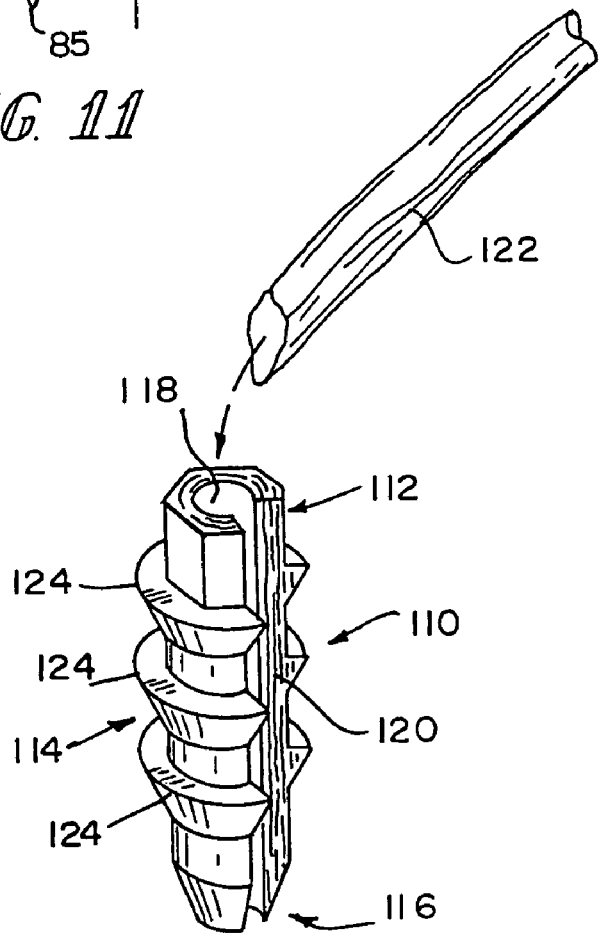
FIG. 9  FIG. 13

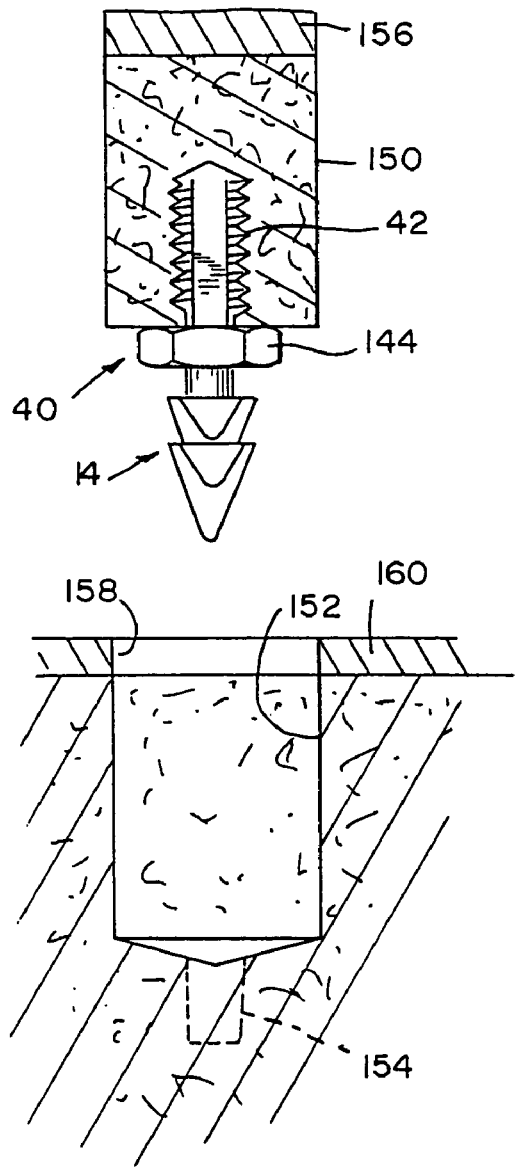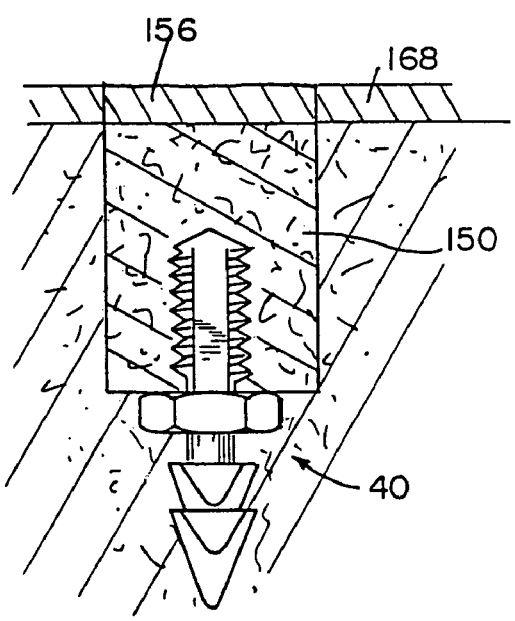
FIG. 17
FIG. 18

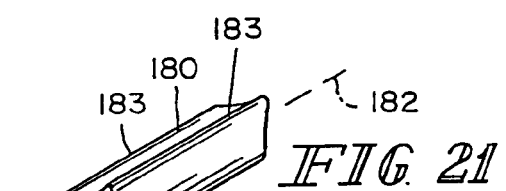
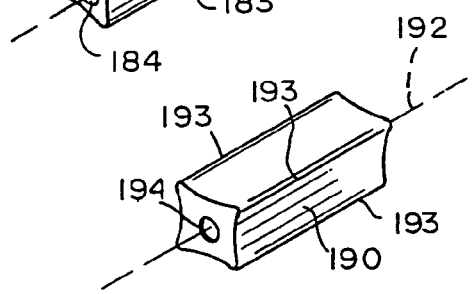
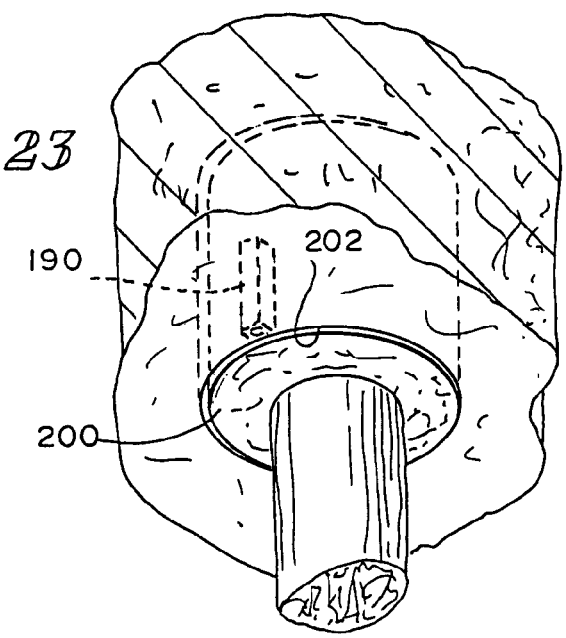
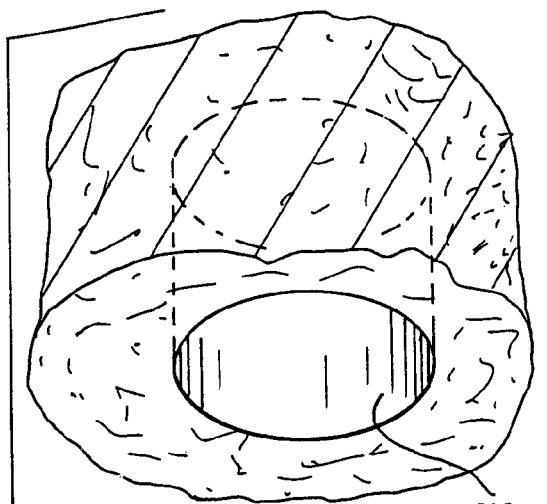
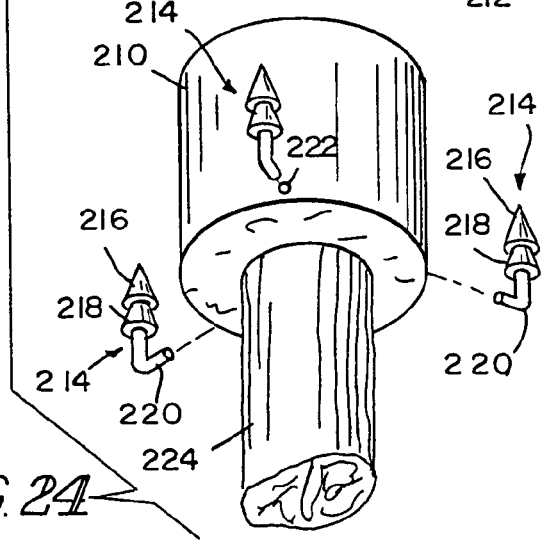
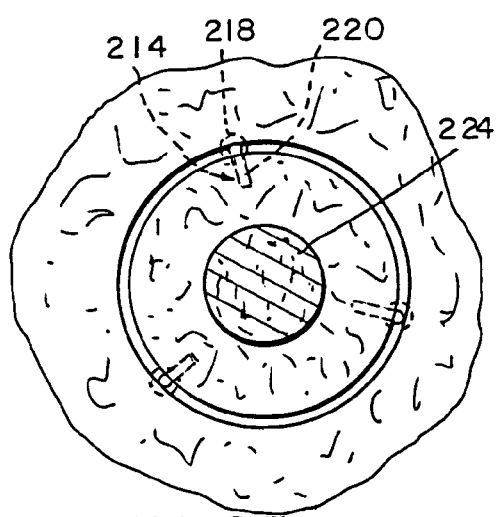

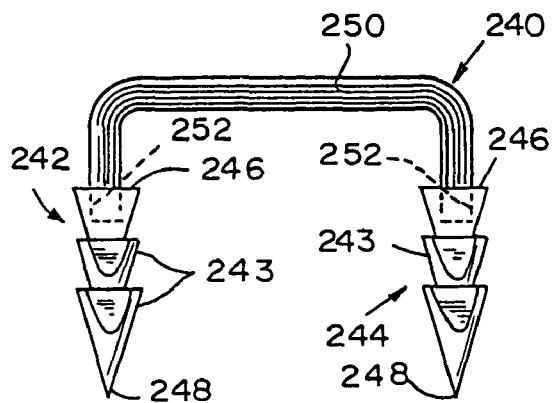
FIG. 26
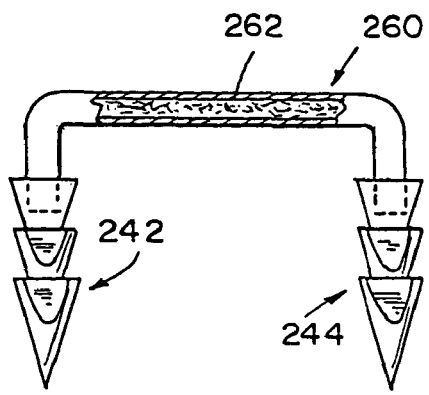
FIG. 27
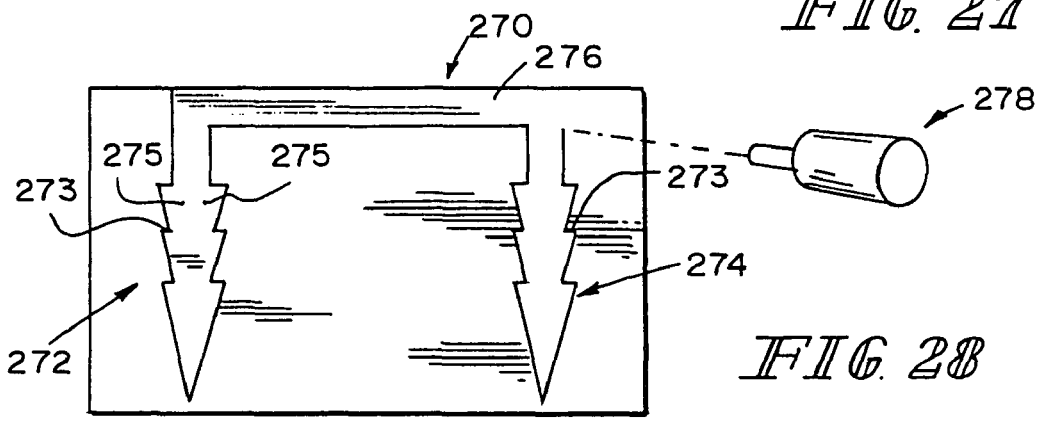
FIG. 28
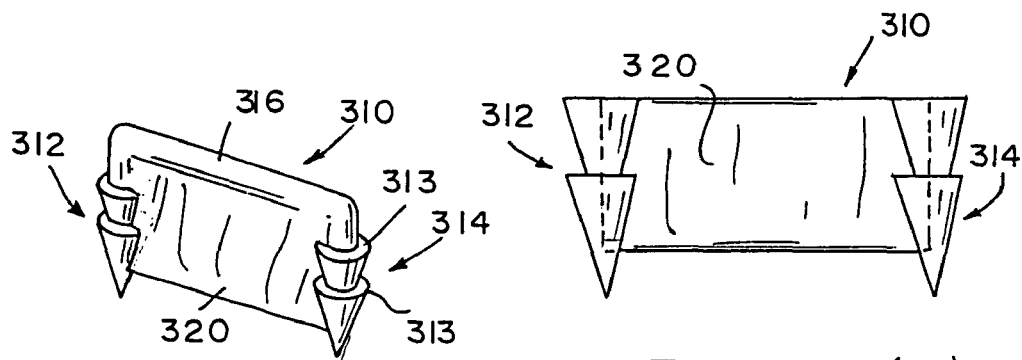
FIG. 29                                   FIG. 29 (a)

DEVICE FROM NATURALLY OCCURRING BIOLOGICALLY DERIVED MATERIALS

CROSS-REFERENCE TO RELATED APPLICATIONS

This application is a U.S. national counterpart application of international application Ser. No. PCT/US02/23189 filed Jul. 15, 2002, which claims the benefit of U.S. provisional applications Ser. Nos. 60/305,786 and 60/389,028 filed Jul. 16, 2001, and Jun. 14, 2002, respectively, and is related to U.S. application Ser. No. 10/195,719 filed Jul. 15, 2002, which also claims the benefit of U.S. provisional applications Ser. Nos. 60/305,786 and 60/389,028 filed Jul. 16, 2001, and Jun. 14, 2002, respectively.

BACKGROUND AND SUMMARY OF THE INVENTION

The present invention relates to devices for attaching, repairing or regenerating orthopedic tissue, particularly to such devices made from naturally occurring extracellular matrix cured or treated to have structural rigidity and hardness.

It is known to use various collagen scaffolds to provide a scaffold for repair and regeneration of damaged tissue. U.S. Pat. No. 6,042,610 to ReGen Biologics, hereby incorporated by reference, discloses the use of a device comprising a bioabsorbable material made at least in part from purified natural fibers. The purified natural fibers are cross-linked to form the device of U.S. Pat. No. 6,042,610. The device can be used to provide augmentation for a damaged meniscus. Related U.S. Pat. Nos. 5,735,903, 5,479,033, 5,306,311, 5,007,934, and 4,880,429 also disclose a meniscal augmentation device for establishing a scaffold adapted for ingrowth of meniscal fibrochondrocyts.

It is also known to use naturally occurring extracellular matrices (ECMs) to provide a scaffold for tissue repair and regeneration. One such ECM is small intestine submucosa (SIS). SIS has been described as a natural acellular biomaterial used to repair, support, and stabilize a wide variety of anatomical defects and traumatic injuries. See, for example, Cook® Online News Release provided by Cook Biotech Inc. at "www.cookgroup.com". The SIS material is derived from porcine small intestinal submucosa that models the qualities of its host when implanted in human soft tissues. Further, it is taught that the SIS material provides a natural scaffold-like matrix with a three-dimensional structure and biochemical composition that attracts host cells and supports tissue remodeling. SIS products, such as OASIS and SURGISIS, are commercially available from Cook Biotech Inc., Bloomington, Ind.

Another SIS product, RESTORE Orthobiologic Implant, is available from DePuy Orthopaedics, Inc. in Warsaw, Ind. The DePuy product is described for use during rotator cuff surgery, and is provided as a resorbable framework that allows the rotator cuff tendon to regenerate. The RESTORE Implant is derived from porcine small intestine submucosa, a naturally occurring ECM (composed of mostly collagen type I (about 90% of dry weight) glycosaminoglycans and other biological molecules), that has been cleaned, disinfected, and sterilized. During seven years of preclinical testing in animals, there were no incidences of infection transmission from the implant to the host, and the RESTORE Implant has not adversely affected the systemic activity of the immune system.

While small intestine submucosa is available, other sources of ECM are known to be effective for tissue remodeling. These sources include, but are not limited to, stomach, bladder, alimentary, respiratory, or genital submucosa, or liver basement membrane. See, e.g., U.S. Pat. Nos. 6,379,710, 6,171,344, 6,099,567, and 5,554,389, hereby incorporated by reference. Further, while SIS is most often porcine derived, it is known that these various submucosa materials may be derived from non-porcine sources, including bovine and ovine sources. Additionally, the ECM material may also include partial layers of laminar muscularis mucosa, muscularis mucosa, lamina propria, stratum compactum and/or other tissue materials depending upon factors such as the source from which the ECM material was derived and the delamination procedure.

For the purposes of this invention, it is within the definition of a naturally occurring ECM to clean and/or comminute the ECM, or to cross-link the collagen within the ECM. It is also within the definition of naturally occurring extracellular matrix to fully or partially remove one or more components or subcomponents of the naturally occurring matrix. However, it is not within the definition of a naturally occurring ECM to extract, separate and purify the natural components or sub-components and reform a matrix material from purified natural components or sub-components. Also, while reference is made to SIS, it is understood that other naturally occurring ECMs (e.g., stomach, bladder, alimentary, respiratory or genital submucosa, and liver basement membrane), whatever the source (e.g., bovine, porcine, ovine) are within the scope of this invention. Thus, in this application, the terms "naturally occurring extracellular matrix" or "naturally occurring ECM" are intended to refer to extracellular matrix material that has been cleaned, disinfected, sterilized, and optionally cross-linked.

The following U.S. patents, hereby incorporated by reference, disclose the use of ECMs for the regeneration and repair of various tissues: U.S. Pat. Nos. 6,379,710; 6,187,039; 6,176,880; 6,126,686; 6,099,567; 6,096,347; 5,997,575; 5,993,844; 5,968,096; 5,955,110; 5,922,028; 5,885,619; 5,788,625; 5,762,966; 5,755,791; 5,753,267; 5,733,337; 5,711,969; 5,645,860; 5,641,518; 5,554,389; 5,516,533; 5,445,833; 5,372,821; 5,352,463; 5,281,422; and 5,275,826. U.S. Pat. No. 5,352,463 discloses an SIS pillow filled with comminuted SIS for regeneration of a meniscus. While U.S. Pat. No. 5,352,463 contemplates the general concept of meniscus regeneration with an SIS filled pouch, it does not address itself to providing such a pouch having the capability of withstanding the compression and shear stresses involved in an implant for regenerating a meniscus. Also, U.S. Pat. No. 5,352,463 does not contemplate placing structural members formed from naturally occurring ECM, where in the ECM is right and hardened.

It is known to use materials such as catgut and SIS to make appliances. See WO 95/06439 to Bolesky. The Bolesky application discloses devices that are semi-rigid and are formed into desired shapes, but Bolesky does not disclose a process for fabricating naturally occurring extracellular matrix parts that are rigid and hardened.

In the present invention, the density and porosity of the extracellular matrix material can be controlled with drying protocols, including air drying, air drying with heat, and air drying with pressure. Thus, the ECM material can be dried to have a hardness sufficient to machine the device, without the need to form the device into the general shape by molding. By managing density and porosity of the ECM, various fixation devices can be made having superior material properties, wherein the devices promote healing while remaining biocompatable and biodegradable.

The present invention, in one of its embodiments, is an orthopedic device for attaching soft tissue such as cartilage, ligaments, and tendons to bone. The device, which in one embodiment has a head end portion configured to engage soft tissue and a body portion configured to engage and attach to the bone, is preferably monolithic and formed as a unitary structure from naturally occurring extracellular matrix. The body portion of the device may illustratively terminate with a pointed end distal from the head portion to facilitate the penetration into the bone. Between the pointed distal end and the head portion, the device may illustratively be formed with radially outwardly extending barbs. These barbs may incline toward the head portion to provide a barbed tack or tack-like device. In some embodiments, a body portion is provided with diametrically opposed flats extending therealong, the flats being generally parallel.

It has been found that a mass of naturally occurring ECM may be cured to be very rigid and hardened so that it can be machined using conventional cutting tools and using laser machining. The devices of this invention may be formed by machining a mass of cured matrix to define the head portion and body portion. The mass may be formed by compressing the ECM into a solid mass. For example, the ECM may be comminuted and formed into a solid mass with interlocking strands of ECM.

For example, a tightly balled or compacted mass of pieces of SIS, illustratively comminuted SIS, can be formed by air drying or by hot air drying to become extremely hard. Unexpectedly, this hardened SIS can be machined or formed to have very sharp pointed ends, sharp barbs, etc. With this process, tacks, barbed tacks, and threaded elements may be machined from such cured mass of SIS. The tacks may be double-ended tacks or may include a central head portion and a sharpened body portion extending axially from each end of the head portion. Alternatively, a device may be made such that one body portion may be threaded while another body portion has barbs.

In one embodiment, such tacks or barbs may be attached to devices made of naturally occurring extracellular matrix laminated together to form a body portion. For example, such a body portion may be fabricated to be placed into the tear of a meniscus to extend along the tear. One or more tacks or barbs made in accordance with the present invention may be coupled to the body portion to secure the device in the tear. Each of these tacks may be made from naturally occurring extracellular matrix cured to be hard and rigid.

A staple or a staple-like device may be fabricated in accordance with the present invention utilizing two or more spaced apart barbs, each having a sharpened distal end and a proximal end. A connecting member may be placed between the proximal ends of the barbs. This connecting member may itself be made from a material such as SIS and optionally may be formed integrally with the barbs. Thus, in accordance with the present invention, an orthopedic staple device may be made from naturally occurring extracellular matrix hardened to have two or more sharpened barbs connected by strands of extracellular matrix such as SIS. In some embodiments of the present invention, such a staple or staple-like device may be made by laminating several layers of naturally occurring extracellular matrix and curing the layers to form a rigid and hardened sheet-like body. The barbs and the connecting member or members are then cut from the body. It has been found that the barbs and connecting member may be cut by laser machining a pattern on the sheet-like body. It has also been found that such barbs may be formed to have edges fused together by the laser machining process.

In another embodiment, a device for anchoring a bone plug in an opening formed in a bone is provided. The device comprises a mass of naturally occurring extracellular matrix formed into a rigid and hardened member configured to be wedged in the opening between the bone plug and the bone. This rigid and hardened member may be formed with outwardly extending barbs to dig into the bone plug and the bone. The device may also have a connecting portion to extend into an opening in the bone plug. In some embodiments, the member is designed to extend axially along side the bone plug, and the member may have a plurality of radially outwardly and longitudinally extending fins to dig into the bone plug and the bone. The elongated member may be cannulated so that it may be guided into place on a guide member such as a K-wire. In some embodiments, the member may be formed in the shape of a screw to be threaded into the opening between the bone plug and the bone.

There is provided, therefore, a method for anchoring a bone plug into an opening formed in a bone for receiving a plug, the method comprising the steps of providing a member formed into a rigid and hardened mass of naturally occurring extracellular matrix and placing the member into the opening between the bone and the bone plug. In some embodiments, the bone opening will be formed with a cylindrical wall and a bottom (or upper end) to receive a cylindrical bone plug, and the placing step will comprise placing the member in the bone plug to engage the bone plug and the bone. The member may be a double-ended tack, one end of which extends into the bottom of the opening and the other end of which extends into the bone plug. The double ended tack may radially expand the plug to engage the wall of the opening.

In another embodiment, a device for attaching a soft tissue such as a tendon, ligament, or ligament replacement has been provided. The device, which is formed from a hardened mass of naturally occurring extracellular matrix, is provided with an elongated body to be received in the opening in the bone. The body has a channel therein for receiving a portion of the soft tissue. This body is configured to collapse inwardly to grip and hold the soft tissue in the channel when the body is inserted into the opening. In some embodiments, the body may be threaded to accomplish inserting the device into the opening. It will be appreciated that such a device may be used for attaching an ACL replacement ligament in a tunnel formed in a femur, wherein the tunnel has an axis and a generally cylindrical wall. Such tunnel formation is known in the ACL replacement art. The body may be provided with a generally axial channel for receiving a portion of the ligament replacement to be attached to the femur, and the body may be formed to collapse inwardly to secure the replacement ligament portion in the channel as the device is threaded in the femur tunnel.

It will be appreciated that, in some embodiments, the naturally occurring extracellular matrix may be cured in such a fashion that the device will provide support structure members for various applications in the orthopedic field. For example, a device for regenerating a meniscus or a portion thereof may be provided with upper and lower panels and a support structure disposed between the upper and lower panels. This support structure may be provided by one or more members of rigid and hardened naturally occurring extracellular matrix. The one or more members may comprise a plurality of generally wedge-shaped members, each member having an upper edge supporting the upper panel and a lower edge supported on the lower panel. In other embodiments, the one or more support members may comprise a lattice of interlocking members, some of which extend radially toward the center of the knee and others of which extend transversely to the radially extending members. These members arranged in the lattice structure define a plurality of spaces between the upper and lower panel. These spaces may be filled with a biological material to promote regeneration of the meniscus. For example, the spaces may be filled with comminuted SIS, a bioactive agent, a biologically derived agent, cells, a biological lubricant, a biocompatible polymer, a biocompatible inorganic material, or combinations thereof. The ECM support structure is believed to provide a framework for meniscus generation. The insertion of the device into a space from which the defective portion of the meniscus has been removed and the attachment of the device to the surrounding tissue places the device such that the meniscus will be regenerated in the space from which the defective portion has been removed. The structural members provided by the rigid and hardened ECM will provide the required support for the joint while regeneration occurs. See U.S. Provisional Patent Application No. 60/305,786, and U.S. patent application Ser. No. 10/195,794 entitled "Meniscus Regeneration Device and Method" (Attorney Docket No. 265280-71141, DEP-745), filed concurrently herewith, each hereby incorporated by reference.

Thus, one aspect of this disclosure is an orthopedic device for attaching soft tissue such as cartilage, ligament and tendons to bone, the device having a head portion configured to engage soft tissue and a body portion configured to engage and attach to the bone, the head portion and body portion being monolithic and formed from naturally occurring extracellular matrix (ECM) cured to be rigid and hardened to facilitate attachment to the bone.

Another aspect of this disclosure is an orthopedic tack comprising a head portion and a first body portion formed from naturally occurring extracellular matrix cured to be hard and rigid.

Yet another aspect of this disclosure is a device for repairing a tear in a cartilaginous surface such as a meniscus, the device comprising strips of naturally occurring extracellular matrix laminated together to form a body portion to be placed down into the tear to extend along the tear, and one or more tacks coupled to the body portion to secure it in the tear, each of the one or more tacks being formed from naturally occurring extracellular matrix.

Still another aspect of this disclosure is an orthopedic device for attaching or repairing tissue, the device comprising two spaced apart barbs, each barb having a sharpened distal end and a proximal end, and a member connecting the proximal ends of the barbs, the barbs being formed from naturally occurring extracellular matrix An additional aspect of this disclosure is a device for anchoring a bone plug in an opening formed in a bone, the device comprising a mass of naturally occurring extracellular matrix formed into a rigid and hardened member configured to be wedged in the opening between the bone plug and the bone.

Another additional aspect of this disclosure is a method for anchoring a bone plug into an opening formed in a bone for receiving the plug, the method comprising the steps of: providing a member formed into a rigid and hardened mass of naturally occurring extracellular matrix, and placing the member into the opening between the bone plug and the bone.

Still another aspect of this disclosure is a device for attaching a soft tissue to a bone that has been prepared with an opening to receive the device, the device being formed from a hardened mass of naturally occurring extracellular matrix to form an elongated body to be received in the opening, the body having a channel therein for receiving a portion of the soft tissue, the body being configured to collapse inwardly to grip and hold the soft tissue portion in the channel when the body is inserted into the opening.

A further aspect of this disclosure is a tack for driving into a bone, the tack having a proximal head end portion, a distal pointed end portion, and an intermediate body portion, the tack being formed from a hardened mass of naturally occurring extracellular matrix.

In yet another aspect of this disclosure a device is provided for regenerating a meniscus or a portion thereof, the device comprising a wedge-shaped body having an upper panel and a lower panel angularly separated to define an apex portion and a base portion, the panels being formed of a naturally occurring extracellular matrix, and a support structure disposed between the upper panel and lower panel, the support structure comprising one or more members of rigid and hardened naturally occurring extracellular matrix.

One more aspect of this disclosure is an orthopedic device comprising a mass of naturally occurring extracellular matrix or naturally occurring bioremodelable collagenous tissue matrix having a hardness greater than 30 HRD on the Rockwell D Scale.

A final aspect of this disclosure is a composite orthopedic device comprising two connected portions, each portion comprising naturally occurring extracellular matrix material or naturally occurring bioremodelable collagenous tissue matrix, each portion having a hardness and a density, wherein one portion is configured for anchoring the device to native tissue and has a hardness of no less than 50 HRD on the Rockwell D Scale and a density greater than 0.5 g/cc, and the other portion has a different configuration, a different hardness and a different density.

BRIEF DESCRIPTION OF THE DRAWINGS

FIG. 9 is a side view of a tack-like device used to hold tissue in an opening formed in a bone;

FIG. 10 is a partially sectioned side view of a tack-like device with a central core filled with comminuted ECM material;

FIG. 11 is a side view of a tack-like device with a design somewhat different from the FIG. 1 design;

FIG. 12 is an end view of the FIG. 11 device looking along the lines 12-12 in FIG. 11.

FIG. 13 is a perspective view of a device configured to collapse on soft tissue as the device As inserted into an opening in a bone;

FIG. 17 is a diagrammatical drawing showing how the device of FIG. 6 may be threaded into a bone plug and then how the bone plug may be inserted into the opening in a bone;

FIG. 18 is a sectional view showing the bone plug of FIG. 17 installed in the bone with the double-ended device of FIG. 6;

FIG. 21 shows an elongated and cannulated device which has a generally triangular cross-section with relatively sharp side edges to be driven between a bone plug and an opening in which the plug is inserted.

FIG. 22 is a perspective view of a device similar to the FIG. 21 device except that it has a generally square cross-section with four relatively sharp side edges;

FIG. 23 shows a perspective view of how the devices of FIGS. 21 and 22 may be driven to wedge between a bone plug and a bone opening to anchor the bone plug;

FIG. 24 shows a device using barbs made in accordance with the present invention to hold a bone plug into an opening formed in the bone;

FIG. 25 shows an end view of the bone plug of FIG. 24 inserted into the bone opening;

FIG. 26 shows a staple-like device made in accordance with the present invention.

FIG. 27 shows a variation on the staple-like device of FIG. 26;

FIG. 28 shows how a staple-like device may be cut from laminated layers of ECM material;

FIG. 29 shows a laminated body of ECM material held in position by tack-like devices;

FIG. 29(a) shows the device of FIG. 29 without a connecting member between the tacks;

DETAILED DESCRIPTION OF THE DRAWINGS

Figure 1:
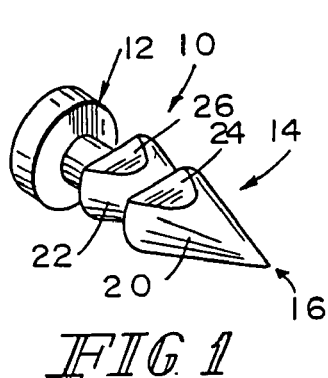
FIG. 1 is a perspective view of an orthopedic device for attaching soft tissue such as cartilage, ligaments and tendons to bone, the device having a head portion configured to engage the soft tissue and a body portion configured to engage and attach to the bone.
Figures 2, 3:
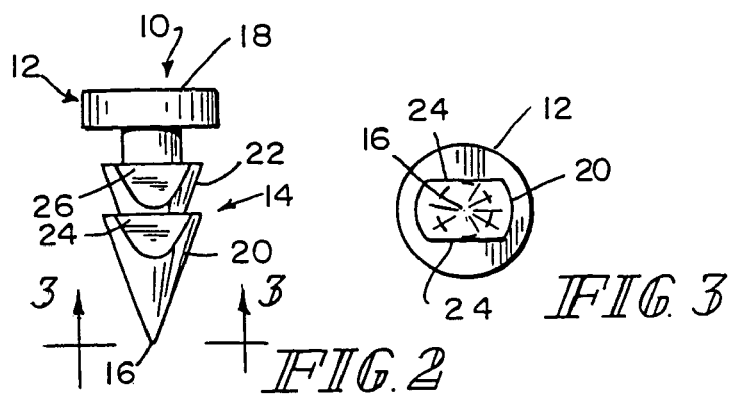
FIG. 2 is a side view of the device of FIG. 1.
FIG. 3 is an end view of the device looking along the lines 3-3 in FIG. 2.

FIGS. 1-3 show an orthopedic device 10 for attaching soft tissue such as cartilage, ligaments, tendons to bone, the device having a head portion 12 configured to engage soft tissue and a body portion 14 configured to engage and attach to the bone. The head portion 12 and body portion 14 are illustratively monolithic and formed from naturally occurring extracellular matrix cured to be rigid and hardened to facilitate attachment to the bone. The body portion 14 terminates with a pointed end 16 distal from the head portion 12 to facilitate penetration into the bone. It will be appreciated that the ECM material from which the device 10 is fabricated will be cured to be hardened and toughened such that the device 10 may be driven into bone tissue. The pointed end 16 with its hardness and toughness will facilitate insertion into the bone. To enhance the holding or gripping ability of the device 10, the body portion 14, between the pointed end 16 and the head portion 12, is provided with radially outwardly extending barbs or barb portions 20, 22, which are illustratively inclined toward the head portion. These portions 20, 22 are illustratively defined by machining or forming diametrically opposed flats 24, 26 on the body portion 14, the flats being generally parallel. As best seen in FIG. 3, flats 24 are formed on diametrically opposite sides of the barb portion 20 while the flats 26 are formed on the diametrically opposite sides of the barb portion 22.

The device of FIGS. 1-3 and other similar devices disclosed herein may be fabricated by compacting comminuted or shredded naturally occurring ECM material into bar or rod stock by curing the material such that it is very rigid and hardened. The curing may be accomplished by air drying comminuted ECM at room temperature for several days. Comminuted ECM, when dried at room temperature for several days, becomes very tough and hard and can be machined using conventional tools. In one example, a sample of 3 cc of comminuted SIS that has been air dried at room temperature for several days produced a piece of SIS stock that is 7-8 mm in diameter and 2 mm thick, and has a hardness of about 70 HRD on the "Rockwell D" scale. For comparison, polyethylene tests at about 30 HRD, and plexiglass is between 70 and 75 HRD on the "Rockwell D" scale (ASTM D2240, Vol. 0991). Testing was done using an e2000 series durometer from PTC Instruments (model 502D). This durometer conforms to the ASTM D2240 type D standard. The indentor in this type (as in all durometers conforming to ASTM D2240 type D) is a sharp point indentor with a 30 degree included angle and applies a force of 4536 gmf on the sample being tested.

Thus, in an illustrated embodiment an orthopaedic device is formed from comminuted SIS that has been air dried at room temperature for several days. The SIS has a hardness of at least 30 HRD on the "D" scale, particularly at least 50 on the "D" scale, more particularly above 60 HRD on the "D" scale, and most particularly about 70 HRD or above on the "D" scale. A hardness of 60-70 is usable in many applications.

One sample of comminuted and air-dried SIS was found to have a density of 0.747+/−0.059 gm/cc. For comparison, the density of the commercially available RESTORE® product, an ECM laminate, is 0.466+/−0.074 gm/cc. And, an ECM product consisting of toughened SIS laminate as described in "Meniscus Regeneration Device and Method" (provisional U.S. Patent Application No. 60/305,786 filed on Jul. 16, 2001, and U.S. patent application Ser. No. 10/195,794 entitled "Meniscus Regeneration Device and Method", filed concurrently herewith, has been made with a density of 0.933+/−0; 061 gm/cc; and an SIS foam can be made as described in U.S. patent application Ser. No. 10/195,606 entitled "Cartilage Repair and Regeneration Device and Method", filed concurrently herewith and hereby incorporated by reference, with a substantially lower density: 0.091+/−0.019 gm/cm$^3$; 0.035+/−0.012 gm/cm$^3$; or 0.006+/−0.002 gm/cm$^3$, for example.

Drying and hardening may be accelerated by using heat and/or pressure. In an illustrated embodiment, the ECM may be comminuted using a COMITROL machine from Urschel Laboratories (Valparaiso, Ind.), with a Vericut sealed impeller at 9391 rpm.

Once the bar stock or rod stock is provided, it may be machined with conventional machine shop equipment to the desired shapes. For example, the device 10 may be turned on a lathe or similar equipment to produce the head portion 12 and the body portion 14 with its generally conical barb portions 20, 22. Then, illustratively, the flats 24, 26 may be separately machined such that the conical portions 20, 22 will become more barb-like. It will be appreciated that various barb configurations may be formed on the device 10, for example, by cutting longitudinally extending slots in the body portion 14 to provide more radially outwardly barbs inclined axially toward the head portion 12.

It has been found that tacks or tack-like devices may be made as shown in FIGS. 1-3 such that they can be driven into bone tissue to be securely anchored in the tissue. The head portion 12 of such devices 10 may trap soft tissue against the bone surface. It will be appreciated that the head portion 12 may have a larger diameter than proportionately shown in FIGS. 1-3 and that the head portion 12 may have a shape other than the circular shape depicted in FIGS. 1-3. The head portion 12 itself may be provided with a roughened or barbed surface facing end 16 to attach to the soft tissue being anchored. It will be appreciated that a plurality of devices 10 may be used to secure soft tissue to bone.

Figure 4:
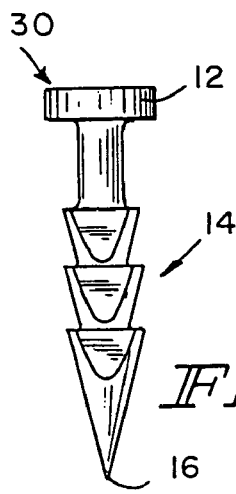
FIG. 4 is a side view of a device similar to the FIG. 1 device except that it is elongated.

FIG. 4 shows a device 30, similar to the device 10 of FIGS. 1-3 except that the device 30 is longer. Throughout this description, some corresponding portions of various devices will be identified with the same reference numerals. For example, the device 30 in FIG. 4 has a head portion 12, a body portion 14, and a pointed distal end 16. The device 30 has three barb portions and three sets of flats. The device 30, of course, is to be driven further into the bone structure than the device 10.

Figure 5:
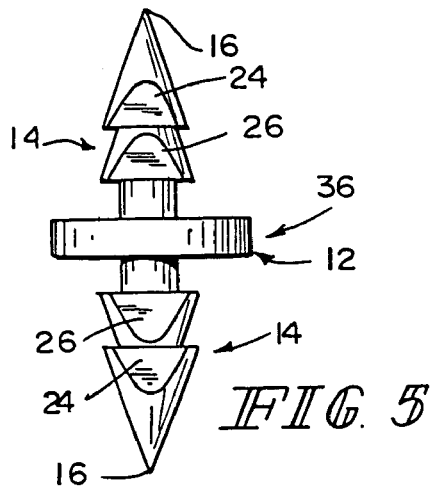
FIG. 5 is a side view of the double-ended tack device.

FIG. 5 shows a device 36 which is essentially a double-ended tack, each end of which is similar to the device 10 with a common head portion 12, having an illustrative proportionately larger diameter than the head portion 12 of FIGS. 1-3. The device 36 of FIG. 5 is provided so that one of its body portions 14 may be inserted into one bone or tissue structure while the other body portion 14 may be inserted into another bone or tissue structure. The diameter of the head portion 12 of the device 36 may be made smaller or larger depending on the attachment application.

Figure 6:
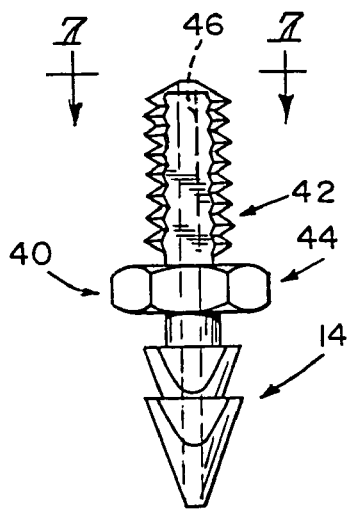
FIG. 6 is a side view of a double-ended device, one end configured as a tack with barbs and the other end being threaded.
Figure 7:
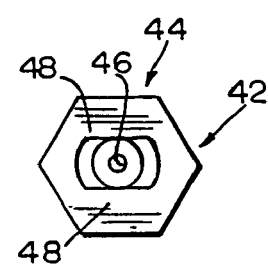
FIG. 7 is an end view of the device shown in FIG. 6 looking along the lines 7-7.

FIG. 6 shows a device 40 which is a double-ended device similar to device 36 of FIG. 5 except that one body portion 42 is threaded. Illustratively, the device 40 has another body portion 14 similar to the body portion 14 of FIGS. 1-3, with a threaded opposite end portion 42. The head portion 44 of the device 40 may be hexagonal as illustrated or otherwise formed to provide a drive portion for inserting the device. It will be appreciated that a surgeon will be provided with a tubular socket to receive and drivingly engage the head portion 44. The illustrative device 40, which may be cannulated as indicated at broken lines 46 so that the device 40 may be accurately positioned on a K-wire, may optionally have its threaded end provided with diametrically opposed flats 48 (FIG. 7). These flats 48 serve to impede rotation subsequent to implantation.

One use of the device 40 shown in FIGS. 6 and 7 will be discussed in conjunction with inserting bone plugs in connection with FIGS. 17 and 18.

Figure 8:
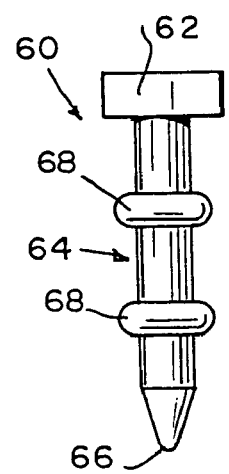
FIG. 8 is a side view of an elongated tack-like device.

FIG. 8 shows a tack 60 with a head portion 62 and an elongated body portion 64 having a distal end 66 that is somewhat sharpened to a point. The tack 60 in FIG. 8 is provided with a pair of longitudinally spaced apart, circumferential ridges 68 between the distal end 66 and the head portion 62. These circumferential ridges 68 serve to lock the device into the surrounding native tissue (i.e., bone).

A device 70 shown in FIG. 10 is similar to devices 10 and 30 except that the proximal body portion 72 including the head 74 is formed with a central bore or opening 76 which may be filled with a mass of comminuted naturally occurring ECM. This central bore space 76 in the device 70 is therefore filled with a biological material to provide a framework for more rapid resorption.

A device 80 is shown in FIGS. 11 and 12 to have a head portion 82, a body portion 84 with a distal sharpened end 85. It will be appreciated that the device 80 is similar to the prior devices except that body portion 84 is formed to have three angularly spaced rows of barbs 86 formed at least in part by three angularly spaced apart, longitudinally extending grooves 88 best seen in FIG. 12. It will be appreciated that the barbs 86 are formed to extend radially outwardly from the body portion 84 and inclined axially toward the head portion 82. These barbs 86 and the barbs 20, 22 in the above-described devices 10, 30, 36, 40 and 70 illustratively have an abrupt or sharp edge facing the head portions of the device. It will be appreciated that when the devices are inserted into a bone, the bone will close in on the body portions and these abrupt axially outwardly facing edges of the barbs to secure the devices in the bone. The head portion 82 is shown having three angularly spaced notches 90, which are provided to aid in grasping in delivery of the device. Other configurations are within the scope of this invention.

In accordance with the present invention, a tack or tack-like device may be provided as shown in FIG. 9 without a head portion. FIG. 9 illustrates a device 96, which may be cannulated as indicated at broken lines 98, for insertion in the bone to hold soft tissue. As with devices 10, 14, and 70, device 96 is provided with a plurality of barbs 92, 93, 94. The device as shown in FIG. 9 illustratively may be used, for example, as an interference screw for wedging a bone plug into a bone tunnel, such as for fixing a replacement ligament into the bone tunnel.

The designs shown in FIGS. 1-9, therefore, provide an orthopaedic tack or barbed tack fabricated from naturally occurring ECM that has been cured to be hard and rigid. These devices 10, 30, 36, 40, 60, 70, 80, and 96 may be fabricated from SIS which is cured to be hard and rigid by comminuting the SIS and allowing the comminuted SIS to air dry.

Figure 15:
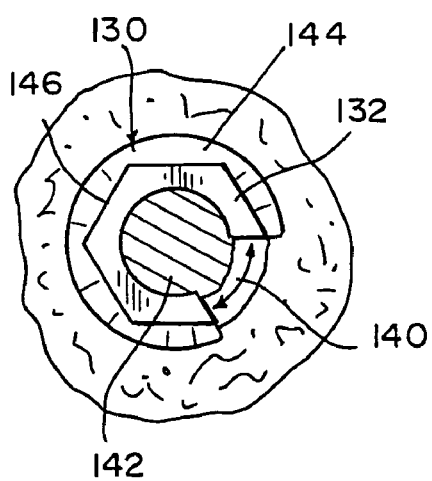
FIG. 15 is a top view of the FIG. 16 device looking along the lines 15-15 in FIG. 16.
Figure 14:
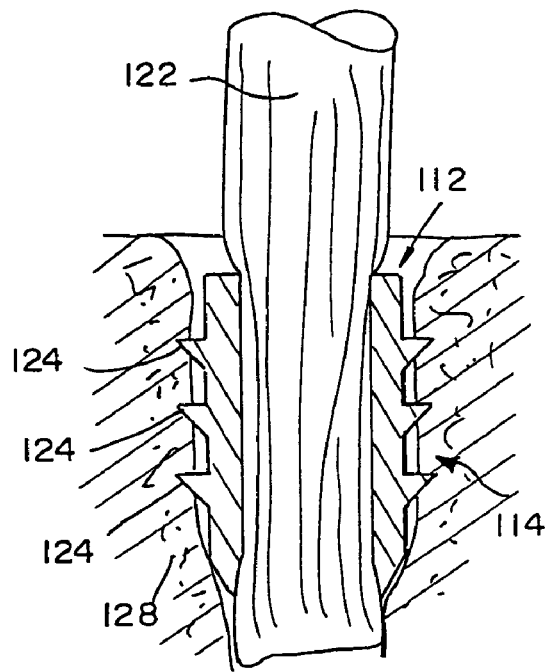
FIG. 14 shows the device of FIG. 13 inserting soft tissue into bone.

A device 110 is provided for attaching a soft tissue such as a ligament or a tendon to a bone is shown in FIG. 13-15, the device being formed from a hardened mass of naturally occurring ECM to have an elongated body to be received in an opening formed in the bone. The device 110 has a head portion 112, a central body portion 114 and a distal end 116 all shaped and configured for insertion into a bone opening having a diameter smaller than the largest diameter of the central body portion 114. The device 110 is also provided with a central, longitudinal extending channel 118 extending axially through the device. The illustrative device 110 is further formed with axially and radially extending cut-out or slot 120 which opens from the channel 118 to the exterior of the device 110. It will be appreciated that a piece of soft tissue which may be a ligament, a tendon, or a ligament graft such as an ACL graft, may be inserted axially into the channel 118 to be carried with the device 110 into the bone. While the device 110 is formed from a hardened mass of naturally occurring ECM, it is configured for being forced into an opening prepared in a bone, and to collapse inwardly to grip the soft tissue 122 in the channel 118. The interior of the channel 118 may be provided with a roughened texture or even interior barbs or gripping surfaces to grip the soft tissue 122 more securely as the device 110 collapses radially inwardly. Central body portion 114 is provided with three radially outwardly extending frustoconical engagers 124 which serve to anchor the device 110 in the bone. These engagers 124 have outer surfaces which incline axially toward the head portion 112 and radially outwardly. As the device 110 is driven into the bone opening, these engagers 124 will cause the device to collapse inwardly by bringing the longitudinal walls of the cut-out 120 closer together, reducing the diameter of the channel 118, and holding soft tissue 122 securely within bone 128, as shown in FIG. 14. The engagers 124, as illustrated in FIG. 13, have abrupt radially outwardly extending and axially facing surfaces for anchoring the device 110 in the bone opening.

Figure 16:
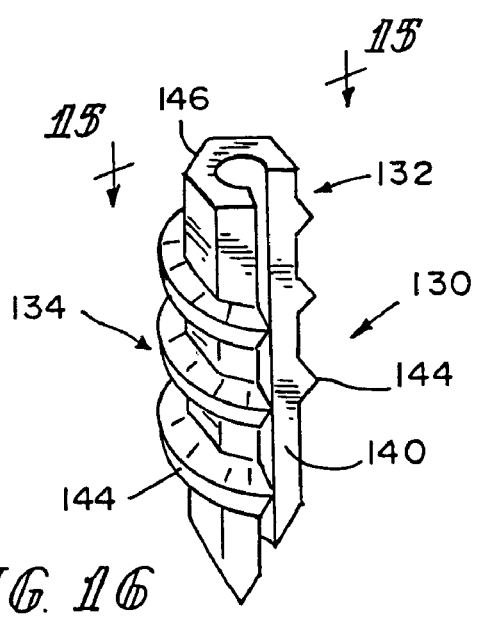
FIG. 16 is similar to the FIG. 13 device with helical thread segments to facilitate threading the device into an opening in a bone.

It will be appreciated that the device 130 may be formed as a threaded device as shown in FIG. 15-16 with helical thread segments replacing the engagers 144 on the central body portion 134. When the device 130 is so threaded, and the head end portion 132 with the hex-shaped cuts 146 is engaged with a socket driver, with the driver end preferably formed on a tube for receiving the soft tissue graft 142, the device 130 can be threaded into a bone opening.

FIGS. 17 and 18 show diagrammatically how the device 40 of FIGS. 6 and 7 can be used to anchor a bone plug 150 into an opening 152 drilled or otherwise formed in a bone. The threaded body portion 42 of the device 40 may be threaded into a central opening in the bone plug 150 as depicted in FIGS. 17 and 18. The opening 152 in the bone may be provided at a diameter which will snugly receive the bone plug 150. The barbed portion (body portion 14) of device 40 is provided to anchor into the bottom of the opening 152. It may be advantageous to provide a central pilot hole 154 in the bottom of the opening 152 to receive and guide the body portion 14 of the device 40. When the bone plug 150 is forced into the opening 152, the structure shown in FIG. 18 will result with the device 40 anchoring the bone plug 150 in the bone.

It is contemplated that the method and device in FIGS. 17 and 18 may be used to anchor a cartilage plug 156 into a bone. Essentially, a defect in the cartilage in the surface of a bone, such as on the condyle of a knee, will be removed by forming the opening 152 for receiving the bone plug 150. A cartilage graft 156 will be secured to the bone plug 150 to be used to close the opening 158 made in the cartilage layer 160 in the bone. Thus, the bone plug 150 and the anchoring device 140 may be used to hold a cartilage plug 156 in position in an opening 158 in cartilage 160 such that cartilage plug 156 lies in an essentially contiguous plane with the undamaged surrounding cartilage 168.

Figure 19:
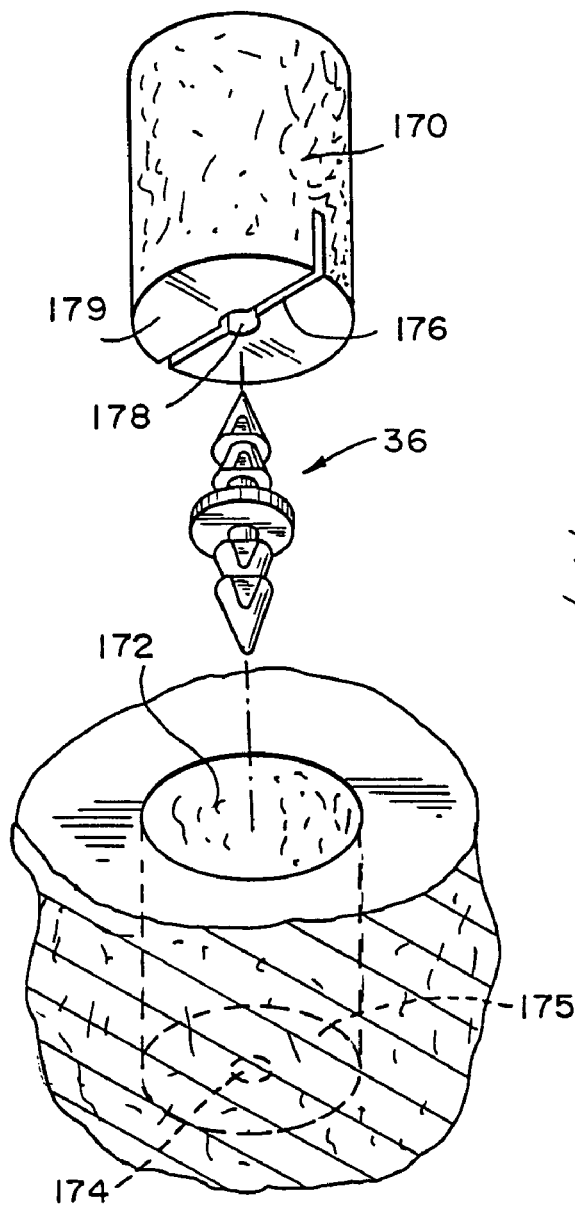
FIG. 19 shows a double-ended tack made in accordance with the present invention used to insert and hold a bone plug into an opening.
Figure 20:
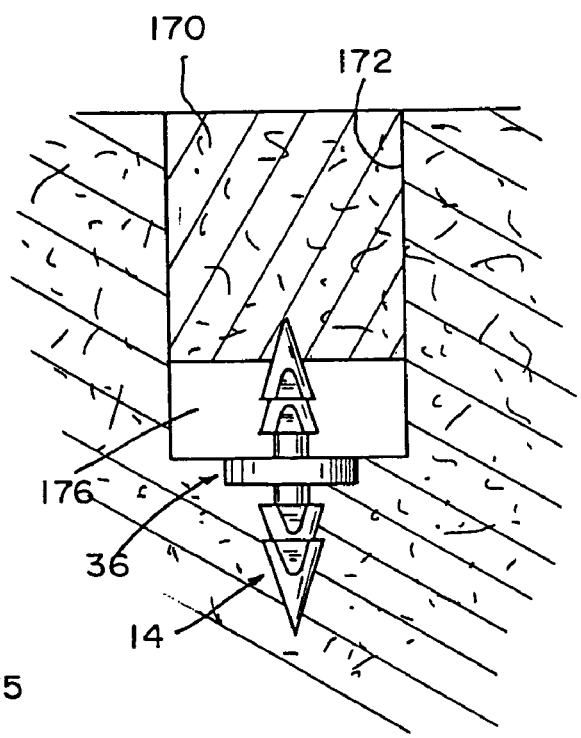
FIG. 20 shows a sectional view of the bone plug of FIG. 19 after insertion.

FIGS. 19 and 20 show how a bone plug 170, which is illustratively formed as a cylindrical bone plug to be anchored into a cylindrical opening 172 in a bone, may be used with the device 36 shown in FIG. 5. The bone opening 172 is provided with a depth sufficient to receive a plug 170, and the bottom 175 of the opening 172 is provided with a pilot hole 174. The plug 170 is prepared with a split end as indicated at 176 and a central pilot opening 178 at bottom surface 179, for facing bottom 175 of opening 172. It will be appreciated that this split end 176 of the bone plug 170 will be wedged outwardly by the device 36 so that the outer surface of the bone plug 170 will firmly engage the internal cylindrical surface of the bone opening 172. FIG. 20 shows the device 36 with one of its end portions 14 anchored into the bone in the bottom of the opening 172.

FIGS. 21 and 22 show devices 180, 190 for use in anchoring bone plugs in openings formed in bones. The devices 180, 190 may be formed from naturally occurring extracellular matrix cured to be rigid and hardened. The device 180 is elongated on a central axis indicated at 182 and may be cannulated on the axis as indicated at 184. Thus, the device 180 may be slid onto a K-wire and located accurately between the outer wall of a bone plug and the inner wall of an opening in which the bone plug is to be anchored. The illustrative device 180 has a generally triangular cross-section providing three longitudinally extending sharpened edges 183 for cutting into the exterior of the bone plug and the interior of the bone opening. Thus, the device 180 may be forced into the space between the exterior of the bone plug and the wall of the opening to extend along the bone plug and wedge the bone plug into firm engagement with the bone opening. The device 190, which is formed about the axis 192 and which may also be cannulated as indicated at 194, is formed to have a generally square cross-section providing four longitudinally extending side edges 193 to cut into the exterior of the bone plug and the interior of the bone opening.

In orthopedic surgery work, there are various reasons to insert a bone plug into an opening formed in a bone. While circular bone plugs and circular bone openings are illustrated and discussed herein, it will be appreciated that bone plugs may take various cross-sectional shapes determined by the instruments used to cut the plugs and the particular surgical need. Typically, it is more convenient to drill a cylindrical opening into a bone for receiving a bone plug. To have the bone plug anchored and secured to the wall of the bone opening, it is often necessary to force the bone plug against the wall of the opening in the host bone so that the required bone nourishment and eventual bone ingrowth may take place. This aspect of anchoring bone plugs to bone openings is well known in the orthopedic field. For example, in ACL surgery, it is known to anchor a bone plug harvested on the end of a patellar tendon strip in a tunnel formed upwardly into the femur. Essentially, the patellar tendon is harvested with a bone plug on one end of the strip. The other end may be provided with a bone plug as well. This patellar strip is then used as an ACL graft replacement. A tunnel is formed upwardly through a tibial platform into the femur and the ACL graft is secured in place by anchoring one of the bone plugs in the femur and the other of the bone plugs in the tibia. Conventionally, cannulated screws are threaded into the openings to extend alongside the bone plugs. These screws thread into the bone plugs and into the walls of the tunnels to push the plugs into engagement with the tunnel walls. The devices 180, 190 are provided as alternatives to the threaded screws. These devices are pushed into the space between the exterior of a wall of the bone plug and the interior wall of the bone opening. Such a configuration is shown in FIG. 23 where the bone plug 200 is illustrated inserted into the opening or tunnel 202. Again, while the plug 200 is illustrated as having a cylindrical cross-section, it will be appreciated that the plug 200 will have a cross-sectional shape defined by the cutting tools used to remove the plug 200 from its original position. The device 190, however, will be inserted into the space between the plug 200 and the wall of the opening 202 to force the plug against the wall of the opening. It is understood that FIG. 23 shows only a portion of a ACL graft attached to the plug 200.

Referring to FIGS. 24 and 25, it will be seen that a bone plug 210 may be secured in a tunnel 212 by barbed anchors 214. Each of these barbed anchors 214 may be formed from hardened naturally occurring ECM to have sharp barbs 216, 218 with a connector portion 220 having a right angle extension 220 to be received into an opening 222 in the bone plug 210. Thus, the barbed anchors 214 may be attached to the bone plug 210 to extend along side the bone plug as it is inserted into the tunnel 212. An ACL graft may be attached to the bone plug 210 as indicated at 224.

The devices are made from ECM that has been cured to a hardness to allow machining. Each of these devices retains its structural integrity for a sufficient period of time to allow the intended orthopaedic fixation, and to permit bone or cartilage ingrowth or repair to begin. Preferably, the devices such as devices 180, 190 and anchors 214 in FIGS. 23-25 as well as the devices 10, 30, 36, 40, 60, 70, 80, 96, and 110 are designed to be absorbed into the host tissue, bone, or soft tissue into which they are placed.

Referring to FIG. 26, it will be seen that an orthopedic device 240 for attaching or repairing tissue is illustrated, the device 240 comprising two spaced apart barb portions 242, 244, each of which has a proximal end portion 246, a sharpened distal end portion 248, and at least one barb 243. The device 240 has a connecting member 250 extending between the proximal ends 246 to provide a staple-like device. Each of the barb portions 242, 244 may be formed as previously discussed from hardened and rigid naturally occurring ECM. The entire device 240 may be machined from a single block of hardened ECM. Alternatively, barb portions 242, 244 and connecting member 250 may be machined separately, and the connecting member 250 may have its ends inserted into and joined into the proximal end portions 246 of the barb portions as indicated at 252. Connecting member 250 may be affixed to the barb portions 242, 244 in any number of ways, including threading or gluing at insertion 252. The device 240, therefore, may be used as a staple, for example, with the barb portions 242, 244 inserted into the bone and the connecting member 250 holding tissue to the bone. The connecting member 250 may be formed from hardened naturally occurring ECM, flexible ECM, or another material.

FIG. 27 shows a device 260 with similar spaced apart barb portions 242, 244 and a connecting member 262 which is hollow and filled with comminuted SIS.

FIG. 28 shows an approach for making a staple or staple-like device 270 having spaced apart barb portions 272, 274 and a connecting member 276. The device 270 contemplates that a plurality of layers of naturally occurring ECM material will be laminated together to be cured by air drying to form a rigid and hardened plate-like body. Then, a laser machine unit 278 will be programmed to cut a pattern which will produce a device 270 from the laminated layers of ECM. It has been found that such laser cutting of several layers of ECM will produce barb portions 272, 274 having cut edges which are sealed and fused together to enhance the attachment capability of the barbs 273. Device 270 may optionally have a plurality of laser cut holes 275, which further fuse together the layers of ECM.

Figure 31:
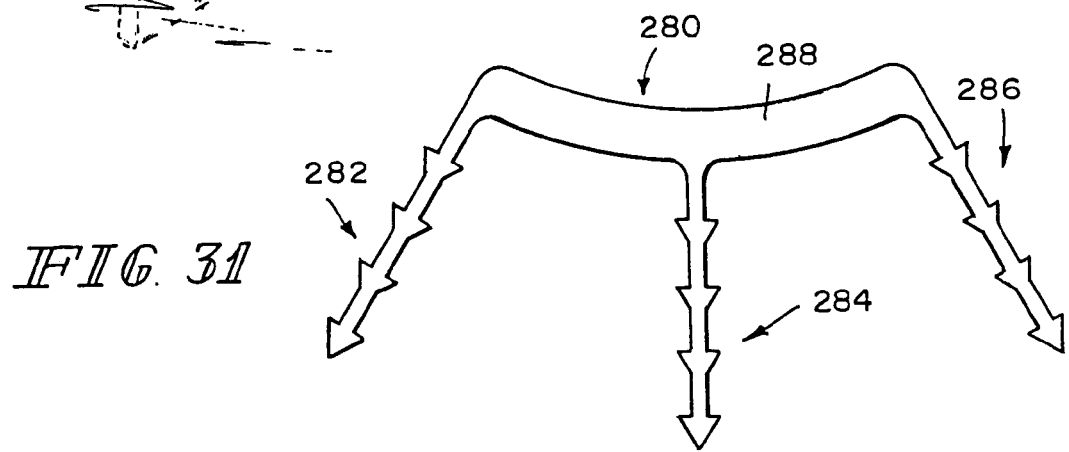
FIG. 31 shows a three-barbed staple device which may be cut from laminated layers of ECM material to have a desired pattern.
Figure 32:
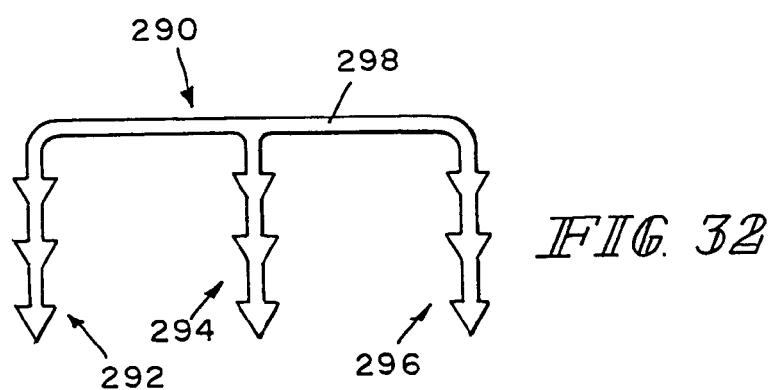
FIG. 32 shows a device similar to FIG. 31, but having a different pattern.

FIGS. 31 and 32 show devices 280 and 290, respectively, with different patterns cut from such laminated layers of rigid and hardened naturally occurring ECM. The device 280 is shown having three spaced apart barb portions 282, 284, 286 with a bowed or curved connecting member 288 extending between the proximal ends of the barb portions. The device 290 in FIG. 32 is shown as having three spaced apart barb portions 292, 294 and 296 with a member 298 connecting the proximal ends of the barbs. Illustratively, the barb portions 282, 284, 286 and the connecting member 288 may all lie in a common plane. Alternatively, the connecting member 288 may be warped or curved so that the barb portions 282, 284, 286 do not necessarily lie in a common plane. In the device 290, the barb portions 292, 294, 296 initially start out being parallel and lying in a common plane. It will be appreciated that the connecting member 298 may be manipulated by the surgeon to relocate the direction of the barb portions 292, 294, 296.

FIG. 29 shows the staple-like device 310 comprising a pair of spaced apart barb portions 312, 314 formed as discussed above. These barb portions 312, 314 are connected by a connecting member 316 extending between the proximal ends of the barb portions. The device 310 comprises strips of naturally occurring ECM laminated together to form a body portion 320 to be placed down into a tear in a cartilaginous surface such as a meniscus. The barbs 313 hold the body 320 in the tear. It is contemplated that the ends of the body 320 will be attached securely to the barb portions 312, 314. One method of attaching body 320 to barb portions 312, 314 is to insert edges of the body 320 into slots provided in body portions 312, 314. Illustratively, the barbs may be provided with a slit for receiving and gripping and holding the ends of the body 320. It is contemplated that, once the device 310 is fully inserted in the meniscus tear and attached with the barb portions 312, 314, the connecting member 31.6 and the upper ends of the barb portions may be cut away leaving a structure such as that shown in FIG. 29(a). The body portion 320 may have characteristics different from those of the barb portions 312, 314. For example, the body portion 320 may have a greater porosity or lower density or lower hardness than the barb portions, and may have characteristics similar to those of commercial products like the RESTORE patch, for example. It should be understood that these possible differences in characteristics are provided by way of example only; the illlustrated embodiments are not intended to limit the material for the body portion 320.

Figure 30:
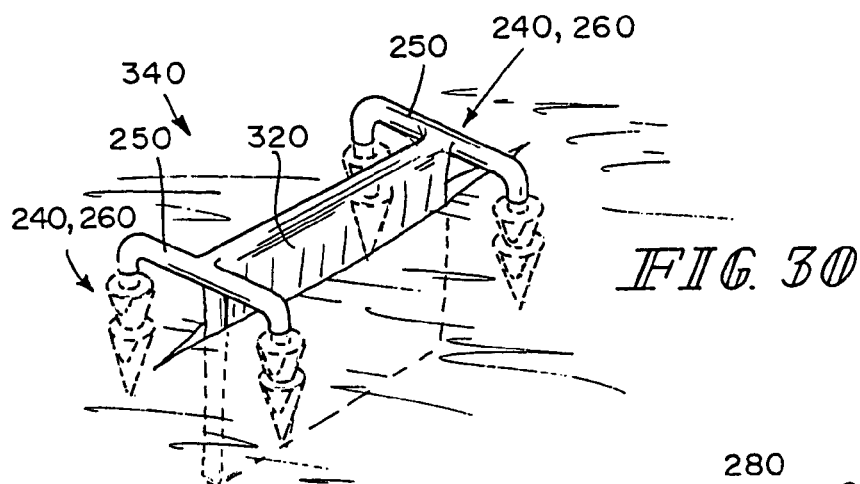
FIG. 30 shows a perspective view of staple-like devices shown in FIGS. 26 and 27 used to hold a sheet-like body of ECM material in a tear in a meniscus.

FIG. 30 shows a device 340 comprising a body such as the body 320 made from laminating layers of naturally occurring ECM together. The ends of the body 320 in the device 340 are attached to the connecting members 250 similar to two devices 240 or 260 as shown in FIGS. 26 and 27.

It is anticipated that the hardened ECM devices of the present invention can be combined with one or more bioactive agents (in addition to those already present in naturally occurring ECM), one or more biologically derived agents or substances, one or more cell types, one or more biological lubricants, one or more biocompatible inorganic materials, one or more biocompatible synthetic polymers and one or more biopolymers. Moreover, the hardened ECM devices of the present invention can be combined with devices containing such materials.

"Bioactive agents" include one or more of the following: chemotactic agents; therapeutic agents (e.g., antibiotics, steroidal and non-steroidal analgesics and anti-inflammatories, anti-rejection agents such as immunosuppressants and anti-cancer drugs); various proteins (e.g., short chain peptides, bone morphogenic proteins, glycoprotein and lipoprotein); cell attachment mediators; biologically active ligands; integrin binding sequence; ligands; various growth and/or differentiation agents (e.g., epidermal growth factor, IGF-I, IGF-II, TGF-β I-III, growth and differentiation factors, vascular endothelial growth factors, fibroblast growth factors, platelet derived growth factors, insulin derived growth factor and transforming growth factors, parathyroid hormone, parathyroid hormone related peptide, bFGF; TGF$_\beta$ superfamily factors; BMP-2; BMP-4; BMP-6; BMP-12; sonic hedgehog; GDF5; GDF6; GDF8; PDGF); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids. If other such substances have therapeutic value in the orthopaedic field, it is anticipated that at least some of these substances will have use in the present invention, and such substances should be included in the meaning of "bioactive agent" and "bioactive agents" unless expressly limited otherwise.

"Biologically derived agents" include one or more of the following: bone (autograft, allograft, and xenograft) and derivates of bone; cartilage (autograft, allograft, and xenograft), including, for example, meniscal tissue, and derivatives; ligament (autograft, allograft, and xenograft) and derivatives; derivatives of intestinal tissue (autograft, allograft, and xenograft), including for example submucosa; derivatives of stomach tissue (autograft, allograft, and xenograft), including for example submucosa; derivatives of bladder tissue (autograft, allograft, and xenograft), including for example submucosa; derivatives of alimentary tissue (autograft, allograft, and xenograft), including for example submucosa; derivatives of respiratory tissue (autograft, allograft, and xenograft), including for example submucosa; derivatives of genital tissue (autograft, allograft, and xenograft), including for example submucosa; derivatives of liver tissue (autograft, allograft, and xenograft), including for example liver basement membrane; derivatives of skin tissue; platelet rich plasma (PRP), platelet poor plasma, bone marrow aspirate, demineralized bone matrix, insulin derived growth factor, whole blood, fibrin and blood clot. Purified ECM and other collagen sources are also intended to be included within "biologically derived agents." If other such substances have therapeutic value in the orthopaedic field, it is anticipated that at least some of these substances will have use in the present invention, and such substances should be included in the meaning of "biologically derived agent" and "biologically derived agents" unless expressly limited otherwise.

"Biologically derived agents" also include bioremodelable collagenous tissue matrices. The expressions "bioremodelable collagenous tissue matrix" and "naturally occurring bioremodelable collagenous tissue matrix" include matrices derived from native tissue selected from the group consisting of skin, artery, vein, pericardium, heart valve, dura mater, ligament, bone, cartilage, bladder, liver, stomach, fascia and intestine, tendon, whatever the source. Although "naturally occurring bioremodelable collagenous tissue matrix" is intended to refer to matrix material that has been cleaned, processed, sterilized, and optionally crosslinked, it is not within the definition of a naturally occurring bioremodelable collagenous tissue matrix to purify the natural fibers and reform a matrix material from purified natural fibers. The term "bioremodelable collagenous tissue matrices" includes "extracellular matrices" within its definition.

"Cells" include one or more of the following: chondrocytes; fibrochondrocytes; osteocytes; osteoblasts; osteoclasts; synoviocytes; bone marrow cells; mesenchymal cells; stromal cells; stem cells; embryonic stem cells; precursor cells derived from adipose tissue; peripheral blood progenitor cells; stem cells isolated from adult tissue; genetically transformed cells; a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. If other cells are found to have therapeutic value in the orthopaedic field, it is anticipated that at least some of these cells will have use in the present invention, and such cells should be included within the meaning of "cell" and "cells" unless expressly limited otherwise. Illustratively, in one example of embodiments that are to be seeded with living cells such as chondrocytes, a sterilized implant may be subsequently seeded with living cells and packaged in an appropriate medium for the cell type used. For example, a cell culture medium comprising Dulbecco's Modified Eagles Medium (DMEM) can be used with standard additives such as non-essential amino acids, glucose, ascorbic acid, sodium pyrovate, fungicides, antibiotics, etc., in concentrations deemed appropriate for cell type, shipping conditions, etc.

"Biological lubricants" include: hyaluronic acid and its salts, such as sodium hyaluronate; glycosaminoglycans such as dermatan sulfate, heparan sulfate, chondroiton sulfate and keratan sulfate; synovial fluid and components of synovial fluid, including mucinous glycoproteins (e.g., lubricin), tribonectins, articular cartilage superficial zone proteins, surface-active phospholipids, lubricating glycoptoteins I, II; vitronectin; and rooster comb hyaluronate. "Biological lubricant" is also intended to include commercial products such as ARTHREASE™ high molecular weight sodium hyaluronate, available in Europe from DePuy International, Ltd. of Leeds, England, and manufactured by Bio-Technology General (Israel) Ltd., of Rehovot, Israel; SYNVISC® Hylan G-F 20, manufactured by Biomatrix, Inc., of Ridgefield, N.J. and distributed by Wyeth-Ayerst Pharmaceuticals of Philadelphia, Pa.; HYLAGAN® sodium hyaluronate, available from Sanofi-Synthelabo, Inc., of New York, N.Y., manufactured by FIDIA S.p.A., of Padua, Italy; and HEALON® sodium hyaluronate, available from Pharmacia Corporation of Peapack, N.J. in concentrations of 1%, 1.4% and 2.3% (for opthalmologic uses). If other such substances have therapeutic value in the orthopaedic field, it is anticipated that at least some of these substances will have use in the present invention, and such substances should be included in the meaning of "biological lubricant" and "biological lubricants" unless expressly limited otherwise.

"Biocompatible polymers" is intended to include both synthetic polymers and biopolymers (e.g., collagen). Examples of biocompatible polymers include: polyesters of [alpha]-hydroxycarboxylic acids, such as poly(L-lactide) (PLLA) and polyglycolide (PGA); poly-p-dioxanone (PDO); polycaprolactone (PCL); polyvinyl alcohol (PVA); polyethylene oxide (PEO); polymers disclosed in U.S. Pat. Nos. 6,333,029 and 6,355,699; and any other bioresorbable and biocompatible polymer, co-polymer or mixture of polymers or co-polymers that are utilized in the construction of prosthetic implants. In addition, as new biocompatible, bioresorbable materials are developed, it is expected that at least some of them will be useful materials from which orthopaedic devices may be made. It should be understood that the above materials are identified by way of example only, and the present invention is not limited to any particular material unless expressly called for in the claims.

"Biocompatible inorganic materials" include materials such as hydroxyapatite, all calcium phosphates, alpha-tricalcium phosphate, beta-tricalcium phosphate, calcium carbonate, barium carbonate, calcium sulfate, barium sulfate, polymorphs of calcium phosphate, sintered and non-sintered ceramic particles, and combinations of such materials. If other such substances have therapeutic value in the orthopaedic field, it is anticipated that at least some of these substances will have use in the present invention, and such substances should be included in the meaning of "biocompatible inorganic material" and "biocompatible inorganic materials" unless expressly limited otherwise.

It is expected that various combinations of bioactive agents, biologically derived agents, cells, biological lubricants, biocompatible inorganic materials, biocompatible polymers can be used with the hardened ECM devices of the present invention.

It is expected that standard disinfection (e.g., 0.15% peracetic acid in 20% ethanol) and sterilization techniques (e.g., electron beam or gamma irradiation) may be used with the products of the present invention. Although it is anticipated that some of the identified additives could be added to the devices prior to terminal sterilization, other additives, such as cells, for example, would be cultured on previously sterilized devices. In addition, some bioactive agents could be added to the devices in the operating room, such as an autograft of PRP for example.

The hardened ECM devices of the present invention can also be combined with other devices that include naturally occurring ECM, and it is expected that the hardened ECM devices can be combined with purified ECM and commercially available collagen materials and/or with devices that contain purified ECM and commercially available collagen materials.

Illustrative applications for the hardened ECM devices of the present invention, and potential materials to be incorporated with the hardened ECM devices of the present invention, are illustrated in the following U.S. Patent Applications, filed concurrently herewith and incorporated by reference herein in their entireties: Ser. No. 10/195,794 entitled "Meniscus Regeneration Device and Method"; Ser. No. 10/195,347 entitled "Cartilage Repair Apparatus and Method"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; and Ser. No. 10/195,334 entitled "Cartilage Repair and Regeneration Scaffold and Method". Thus, implants can be made as composites of materials of different characteristics.

Although the invention has been described in detail with reference to certain preferred embodiments, variations and modifications exist within the scope and spirit of the invention as described and defined in the following claims.

The invention claimed is:

1. An orthopaedic device comprising a tack for driving into a bone, the tack having a proximal head end portion, a distal pointed end portion, and an intermediate body portion, the tack being made of a hardened mass of comminuted naturally occurring extracellular matrix, wherein the naturally occurring extracellular matrix is selected from the group consisting of small intestinal submucosa, stomach submucosa, bladder submucosa, alimentary submucosa, respiratory submucosa, genital submucosa, and liver basement membrane wherein the naturally occurring extracellular matrix has a hardness of at least 30 on the "D" scale.

2. The device of claim 1 in which the naturally occurring extracellular matrix is small intestinal submucosa.

3. The device of claim 2 in which the small intestinal submucosa has a hardness of at least 50 on the "D" scale.

4. The device of claim 2 in which the small intestinal submucosa has a hardness of at least 60 on the "D" scale.

5. The device of claim 2 in which the small intestinal submucosa has a hardness of at least 70 on the "D" scale.

6. An orthopedic device comprising comminuted naturally occurring extracellular matrix having a hardness greater than 30 HRD on the Rockwell D scale, wherein the naturally occurring extracellular matrix is selected from the group consisting of small intestinal submucosa, stomach submucosa, bladder submucosa, alimentary submucosa, respiratory submucosa, genital submucosa, and liver basement membrane.

7. The orthopedic device of claim 6 wherein the comminuted naturally occurring extracellular matrix has a hardness of at least 60 HRD on the Rockwell D scale.

8. The orthopedic device of claim 6 wherein the comminuted naturally occurring extracellular matrix has a hardness of at least 70 HRD on the Rockwell D scale.

9. The orthopedic device of claim 6 wherein the comminuted naturally occurring extracellular matrix has a density greater than 0.5 g/cc.

10. The orthopedic device of claim 6 wherein the comminuted naturally occurring extracellular matrix has a density greater than 0.7 g/cc.

11. The orthopedic device of claim 6 wherein the device comprises a composite with a material selected from the group consisting of:
   a bioactive agent;
   a biologically derived agent;
   a biological lubricant;
   a biocompatible polymer;
   a biocompatible inorganic material;
   cells;
   chondrocytes;
   osteocytes;
   synoviocytes;
   a naturally occurring bioremodelable collageneous tissue matrix that has a hardness less than 70 HRD on the Rockwell D Scale;
   a naturally occurring bioremodelable collageneous tissue matrix having a density less than 0.7 g/cc;
   a mat including a nonwoven naturally occurring bioremodelable collageneous tissue matrix;
   braided naturally occurring bioremodelable collageneous tissue matrix;
   a foam comprising bioremodelable collageneous tissue matrix;
   a laminate comprising bioremodelable collageneous tissue matrix;
   a woven material comprising bioremodelable collageneous tissue matrix;
   a biologically absorbable polymer laminate;
   a biologically absorbable polymer foam;
   a biologically absorbable polymer woven material; and
   a mat including a nonwoven biologically absorbable polymer.

12. The orthopedic device of claim 6 wherein the device comprises a configuration selected from the group consisting of:
   an orthopedic tack comprising a monolithic head portion and a body portion;
   an anchor for attaching soft tissue to bone, the device having a portion configured to engage soft tissue and an integral portion configured to engage bone;
   an anchor comprising at least two spaced apart barbs, each barb having a sharpened distal end and a proximal end, the device further comprising a member connecting the proximal ends of the barbs;
   an anchor comprising at least two spaced apart barbs and an integral member connecting the two barbs;
   an anchor for anchoring a bone plug in an opening formed in bone, the bioremodelable collageneous tissue matrix being configured to be wedged between the bone plug and the bone;
   an anchor comprising a body having a channel therein, the body being configured to collapse inwardly under compression;
   a outer shell portion and an inner portion surrounded by the shell, wherein the outer shell portion has a hardness greater than 50 HRD on the Rockwell D Scale and the inner portion has a hardness less than 70 HRD on the Rockwell D Scale; and a wedge-shaped body having an upper panel and a lower panel angularly separated to define an apex portion and a base portion, the panels being formed of a naturally-occurring bioremodelable collageneous tissue matrix.

13. The orthopedic device of claim 12 wherein the device comprises a composite with a material selected from the group consisting of:
   a bioactive agent;
   a biologically derived agent;
   a biological lubricant;
   a biocompatible polymer;
   a biocompatible inorganic material;
   cells;
   chondrocytes;
   osteocytes;
   synoviocytes;
   a naturally occurring bioremodelable collageneous tissue matrix that has a hardness less than 70 HRD on the Rockwell D Scale;
   a naturally occurring bioremodelable collageneous tissue matrix having a density less than 0.7 g/cc;
   a mat of nonwoven naturally occurring bioremodelable collageneous tissue matrix;
   a foam comprising bioremodelable collageneous tissue matrix;
   a laminate comprising bioremodelable collageneous tissue matrix;
   a woven material comprising bioremodelable collageneous tissue matrix;
   a biologically absorbable polymer laminate;
   a biologically absorbable polymer foam;
   a biologically absorbable polymer woven; and
   a mat of nonwoven biologically absorbable polymer.

14. The orthopedic device of claim 13 wherein the comminuted naturally occurring extracellular matrix has a hardness of at least 50 HRD on the Rockwell D Scale.

15. The orthopedic device of claim 12 wherein the comminuted naturally occurring extracellular matrix has a hardness of at least 70 HRD on the Rockwell D scale.

* * * * *